(12) United States Patent
Brener et al.

(10) Patent No.: US 11,491,172 B2
(45) Date of Patent: Nov. 8, 2022

(54) COMPOSITIONS AND METHODS OF POTENTIATING ANTIMICROBIALS

(71) Applicant: SciSparc Ltd., Tel Aviv (IL)

(72) Inventors: Ephraim Brener, Rishon Lezion (IL); Elran Haber, Kiryat Ono (IL); Adi Zuloff-Shani, Ramat Hasharon (IL); Ascher Shmulewitz, Tel Aviv (IL)

(73) Assignee: SciSparc Ltd., Tel Aviv (IL)

( * ) Notice: Subject to any disclaimer, the term of this patent is extended or adjusted under 35 U.S.C. 154(b) by 0 days.

(21) Appl. No.: 16/896,701

(22) Filed: Jun. 9, 2020

(65) Prior Publication Data

US 2021/0093652 A1 Apr. 1, 2021

Related U.S. Application Data

(63) Continuation of application No. 16/246,084, filed on Jan. 11, 2019, now abandoned, which is a continuation-in-part of application No. PCT/IL2017/050800, filed on Jul. 13, 2017.

(60) Provisional application No. 62/362,082, filed on Jul. 14, 2016.

(51) Int. Cl.
| | |
|---|---|
| *A61K 31/7036* | (2006.01) |
| *A61K 31/16* | (2006.01) |
| *A61K 31/43* | (2006.01) |
| *A61K 31/352* | (2006.01) |
| *A61K 31/546* | (2006.01) |
| *A61P 31/04* | (2006.01) |
| *A61K 31/065* | (2006.01) |
| *A61K 31/353* | (2006.01) |

(52) U.S. Cl.
CPC ........ *A61K 31/7036* (2013.01); *A61K 31/065* (2013.01); *A61K 31/16* (2013.01); *A61K 31/352* (2013.01); *A61K 31/353* (2013.01); *A61K 31/43* (2013.01); *A61K 31/546* (2013.01); *A61P 31/04* (2018.01); *Y02A 50/30* (2018.01)

(58) Field of Classification Search
None
See application file for complete search history.

(56) References Cited

U.S. PATENT DOCUMENTS

| | | |
|---|---|---|
| 5,506,224 A | 4/1996 | della Valle et al. |
| 6,656,972 B2 | 12/2003 | Calignano et al. |
| 7,348,338 B2 | 3/2008 | Arnold et al. |
| 9,095,563 B2 | 8/2015 | Sekura et al. |
| 2002/0173550 A1 | 11/2002 | Calignano et al. |
| 2005/0054730 A1 | 3/2005 | Fu et al. |

FOREIGN PATENT DOCUMENTS

| | | |
|---|---|---|
| WO | WO 2009/158499 A2 | 12/2009 |
| WO | WO 2010/013240 A1 | 2/2010 |

OTHER PUBLICATIONS

Chakarborty, et al., International Journal of Pharmacognosy and Phytochemical Research, 7:193. (Year: 2015).*
International Search Report dated Oct. 24, 2017, in corresponding PCT International Application.
Katrina Ray; "Adding Weight to the Microbiota's Role in Obesity—Exposure to Antibiotics Early in Life can Lead to Increased Adiposity", Nature Reviews Endocrinology, vol. 8, p. 623, (2012).
Ben-Shabat et al.; "An Entourage Effect: Inactive Endogenous Fatty Acid Glycerol Esters Enhance 2-Arachidonoyl-Glycerol Cannabinoid Activity", European Journal of Pharmacology, pp. 23-31, (1998).
Wagner et al.; "Synergy Research: Approaching a new Generation of Phytopharmaceuticals", Phytomedicine, vol. 16, pp. 97-110, (2009).
Hesselink et al.; "Palmitoylethanolamide: A Natural Body-Own Anti-Inflammatory Agent, Effective and Safe Against Influenza and Common Cold", International Journal of Inflammation, vol. 2013, pp. 1-8, (2013).
Norrby et al.; "The Bacterial Challenge: Time to React", ECDC/EMEA Joint Technical Report, pp. 1-41, (2009).
El-Alfy et al.; Antidepressant-Like Effect of $\Delta^9$-Tetrahydrocannabinol and Other Cannabinoids Isolated from *Cannabis sativa* L.", Pharmacology Biochemistry and Behavior", vol. 95, pp. 434-442, (2010).
Fingl et al.; "The Pharmacological Basis of Therapeutics", Chapter 1, pp. 1, (1975).

* cited by examiner

*Primary Examiner* — Michael Barker
(74) *Attorney, Agent, or Firm* — Finnegan, Henderson, Farabow, Garrett & Dunner, L.L.P.

(57) ABSTRACT

Disclosed herein are pharmaceutical compositions comprising at least one anti-bacterial and at least one cannabinoid and methods of use in treating or preventing bacterial infection or biofilm in a subject in need thereof.

9 Claims, 7 Drawing Sheets

| THC | 0 | 4E-06 | 7.6E-06 | 1.5E-05 | 3E-05 | 6E-05 | 1E-04 | 2E-04 | 5E-04 | 1E-03 | 0.002 | 0.0039 |
|---|---|---|---|---|---|---|---|---|---|---|---|---|
| 0.002 | 0.044 | 0.045 | 0.044 | 0.043 | 0.044 | 0.043 | 0.043 | 0.044 | 0.044 | 0.043 | 0.045 | 0.047 |
| 1E-03 | 0.052 | 0.045 | 0.049 | 0.052 | 0.047 | 0.044 | 0.045 | 0.044 | 0.044 | 0.044 | 0.045 | 0.052 |
| 5E-04 | 0.108 | 0.214 | 0.051 | 0.158 | 0.135 | 0.135 | 0.049 | 0.047 | 0.044 | 0.045 | 0.046 | 0.049 |
| 2E-04 | 0.499 | 0.451 | 0.441 | 0.451 | 0.425 | 0.428 | 0.487 | 0.302 | 0.045 | 0.069 | 0.046 | 0.047 |
| 1E-04 | 0.522 | 0.453 | 0.435 | 0.424 | 0.464 | 0.521 | 0.526 | 0.516 | 0.061 | 0.044 | 0.051 | 0.05 |
| 6E-05 | 0.599 | 0.517 | 0.55 | 0.482 | 0.587 | 0.553 | 0.518 | 0.631 | 0.418 | 0.044 | 0.048 | 0.05 |
| 3E-05 | 0.614 | 0.52 | 0.503 | 0.566 | 0.516 | 0.544 | 0.545 | 0.569 | 0.62 | 0.046 | 0.046 | 0.05 |
| 0 | 0.737 | 0.67 | 0.653 | 0.667 | 0.694 | 0.678 | 0.675 | 0.726 | 0.747 | 0.075 | 0.045 | 0.049 |
| Genta | | | | | | | | | | | | |

Fig. 2

| THC | 0 | 3.8147E-06 | 7.6E-06 | 1.52588E-05 | 3.05176E-05 | 6.10352E-05 | 0.0001 | 0.0002 | 0.0005 | 1E-03 | 0.002 | 0.004 |
|---|---|---|---|---|---|---|---|---|---|---|---|---|
| 0.002 | 0.066 | 0.067 | 0.073 | 0.078 | 0.067 | 0.062 | 0.063 | 0.064 | 0.054 | 0.054 | 0.054 | 0.055 |
| 0.001 | 0.173 | 0.088 | 0.113 | 0.085 | 0.116 | 0.061 | 0.07 | 0.064 | 0.055 | 0.054 | 0.055 | 0.057 |
| 0.0005 | 0.298 | 0.236 | 0.295 | 0.269 | 0.381 | 0.175 | 0.152 | 0.159 | 0.056 | 0.056 | 0.054 | 0.057 |
| 0.0002 | 0.891 | 0.83 | 0.746 | 0.643 | 0.697 | 0.674 | 0.668 | 0.645 | 0.072 | 0.057 | 0.054 | 0.058 |
| 0.0001 | 0.755 | 0.727 | 0.644 | 0.62 | 0.704 | 0.69 | 0.731 | 0.644 | 0.639 | 0.058 | 0.058 | 0.058 |
| 6E-05 | 0.73 | 0.626 | 0.694 | 0.653 | 0.695 | 0.655 | 0.713 | 0.827 | 0.807 | 0.058 | 0.06 | 0.058 |
| 3E-05 | 0.796 | 0.673 | 0.871 | 0.634 | 0.628 | 0.62 | 0.697 | 0.729 | 0.762 | 0.041 | 0.041 | 0.058 |
| 0 | 0.909 | 0.879 | 1.021 | 0.891 | 0.896 | 0.732 | 0.715 | 0.978 | 0.945 | 0.152 | 0.099 | 0.06 |
| Genta | | | | | | | | | | | 0.085 | 0.063 |

Fig. 3

| THC | 0 | 1.5E-05 | 3.1E-05 | 6E-05 | 1E-04 | 2E-04 | 5E-04 | 1E-03 | 0.002 | 0.004 | 0.0078 | 0.016 |
|---|---|---|---|---|---|---|---|---|---|---|---|---|
| 0.125 | 0.047 | 0.044 | 0.04 | 0.044 | 0.044 | 0.043 | 0.042 | 0.043 | 0.042 | 0.044 | 0.052 | 0.064 |
| 0.0625 | 0.104 | 0.158 | 0.153 | 0.092 | 0.047 | 0.046 | 0.044 | 0.043 | 0.043 | 0.045 | 0.058 | 0.062 |
| 0.0313 | 0.75 | 0.567 | 0.626 | 0.587 | 0.53 | 0.414 | 0.044 | 0.044 | 0.044 | 0.046 | 0.051 | 0.063 |
| 0.0156 | 1.156 | 1.055 | 1.027 | 0.988 | 0.929 | 0.866 | 0.389 | 0.043 | 0.049 | 0.046 | 0.06 | 0.067 |
| 0.0078 | 1.172 | 1.112 | 1.054 | 0.965 | 0.952 | 0.966 | 0.89 | 0.043 | 0.045 | 0.048 | 0.051 | 0.062 |
| 0.0039 | 1.195 | 1.087 | 1.11 | 1.042 | 1.072 | 1.028 | 1.049 | 0.431 | 0.043 | 0.045 | 0.053 | 0.062 |
| 0.002 | 1.197 | 1.126 | 1.112 | 1.135 | 1.09 | 1.097 | 1.039 | 0.235 | 0.044 | 0.046 | 0.051 | 0.064 |
| 0 | 1.203 | 1.164 | 1.198 | 1.186 | 1.236 | 1.233 | 1.153 | 0.676 | 0.042 | 0.044 | 0.05 | 0.056 |
| Genta | | | | | | | | | | | | |

Fig. 4

| THC | 0 | 1.5E-05 | 3.1E-05 | 6E-05 | 1E-04 | 2E-04 | 5E-04 | 1E-03 | 0.002 | 0.004 | 0.0078 | 0.016 |
|---|---|---|---|---|---|---|---|---|---|---|---|---|
| 2 | 0.049 | 0.052 | 0.056 | 0.054 | 0.054 | 0.055 | 0.056 | 0.052 | 0.052 | 0.054 | 0.052 | 0.055 |
| 1 | 0.049 | 0.048 | 0.051 | 0.051 | 0.053 | 0.054 | 0.053 | 0.053 | 0.058 | 0.053 | 0.052 | 0.056 |
| 0.5 | 0.049 | 0.048 | 0.05 | 0.053 | 0.052 | 0.052 | 0.052 | 0.051 | 0.051 | 0.052 | 0.052 | 0.059 |
| 0.25 | 0.495 | 0.507 | 0.469 | 0.508 | 0.484 | 0.37 | 0.169 | 0.051 | 0.051 | 0.055 | 0.051 | 0.056 |
| 0.125 | 0.855 | 0.817 | 0.912 | 0.8 | 0.687 | 0.652 | 0.622 | 0.122 | 0.053 | 0.052 | 0.051 | 0.056 |
| 0.0625 | 0.772 | 0.773 | 0.803 | 0.78 | 0.733 | 0.693 | 0.677 | 0.567 | 0.059 | 0.055 | 0.053 | 0.057 |
| 0.0313 | 1.001 | 0.903 | 0.783 | 0.747 | 0.739 | 0.741 | 0.757 | 0.699 | 0.053 | 0.051 | 0.052 | 0.059 |
| 0 | 1.13 | 1.095 | 0.89 | 0.795 | 0.74 | 0.743 | 0.99 | 0.867 | 0.054 | 0.052 | 0.053 | 0.053 |
| Amp | | | | | | | | | | | | |

Fig. 5

| THC \ Carb | 0 | 3.8147E-06 | 7.6E-06 | 1.52588E-05 | 3.05176E-05 | 6.10332E-05 | 0.0001 | 0.0002 | 0.0005 | 1E-03 | 0.002 | 0.004 |
|---|---|---|---|---|---|---|---|---|---|---|---|---|
| 0.0039 | 0.062 | 0.063 | 0.062 | 0.072 | 0.076 | 0.311 | 0.104 | 0.082 | 0.071 | 0.067 | 0.075 | 0.082 |
| 0.002 | 0.073 | 0.071 | 0.081 | 0.076 | 0.12 | 0.073 | 0.08 | 0.076 | 0.075 | 0.079 | 0.071 | 0.071 |
| 0.001 | 0.074 | 0.07 | 0.069 | 0.073 | 0.078 | 0.073 | 0.073 | 0.073 | 0.083 | 0.08 | 0.08 | 0.074 |
| 0.0005 | 0.08 | 0.072 | 0.075 | 0.072 | 0.084 | 0.073 | 0.074 | 0.073 | 0.073 | 0.07 | 0.071 | 0.076 |
| 0.0002 | 0.082 | 0.081 | 0.082 | 0.073 | 0.073 | 0.073 | 0.086 | 0.081 | 0.079 | 0.078 | 0.071 | 0.074 |
| 0.0001 | 0.137 | 0.109 | 0.109 | 0.081 | 0.085 | 0.083 | 0.102 | 0.103 | 0.069 | 0.068 | 0.107 | 0.072 |
| 6E-05 | 0.172 | 0.147 | 0.145 | 0.112 | 0.111 | 0.125 | 0.125 | 0.128 | 0.104 | 0.105 | 0.075 | 0.073 |
| 0 | 0.201 | 0.237 | 0.163 | 0.163 | 0.284 | 0.121 | 0.132 | 0.14 | 0.119 | 0.123 | 0.074 | 0.072 |
| Carb | | | | | | | | | | | | |

Fig. 6

| THC | 0 | 3.8E-06 | 7.6E-06 | 2E-05 | 3E-05 | 6E-05 | 1E-04 | 2E-04 | 5E-04 | 1E-03 | 0.002 | 0.004 |
|---|---|---|---|---|---|---|---|---|---|---|---|---|
| 0.002 | 0.764 | 0.71 | 0.8 | 0.755 | 0.786 | 0.711 | 0.683 | 0.677 | 0.671 | 0.166 | 0.077 | 0.112 |
| 0.001 | 0.788 | 0.729 | 0.711 | 0.733 | 0.694 | 0.725 | 0.653 | 0.695 | 0.691 | 0.411 | 0.074 | 0.069 |
| 0.0005 | 0.84 | 0.707 | 0.76 | 0.759 | 0.746 | 0.71 | 0.696 | 0.73 | 0.754 | 0.812 | 0.085 | 0.076 |
| 0.0002 | 0.813 | 0.743 | 0.725 | 0.768 | 0.738 | 0.777 | 0.782 | 0.718 | 0.689 | 0.814 | 0.078 | 0.072 |
| 0.0001 | 0.832 | 0.766 | 0.734 | 0.735 | 0.71 | 0.665 | 0.773 | 0.743 | 0.715 | 0.755 | 0.673 | 0.072 |
| 6E-05 | 0.854 | 0.812 | 0.806 | 0.736 | 0.702 | 0.723 | 0.761 | 0.798 | 0.839 | 0.841 | 0.769 | 0.073 |
| 3E-05 | 0.839 | 0.777 | 0.768 | 0.734 | 0.72 | 0.711 | 0.689 | 0.793 | 0.832 | 0.766 | 0.826 | 0.07 |
| 0 | 0.924 | 0.873 | 0.787 | 0.843 | 0.862 | 0.852 | 0.837 | 0.882 | 0.815 | 0.997 | 0.802 | 0.079 |
| Genta | | | | | | | | | | | | |

Fig. 7

COMPOSITIONS AND METHODS OF POTENTIATING ANTIMICROBIALS

This application is a continuation of U.S. patent application Ser. No. 16/246,084, filed Jan. 11, 2019, which is a continuation-in-part of International Patent Application No. PCT/IL2017/050800, filed on Jul. 13, 2017, which claims priority under 35 U.S.C. § 119 to U.S. Provisional Application No. 62/362,082, filed on Jul. 14, 2016, each of which is expressly incorporated herein by reference in its entirety.

FIELD

The present invention relates to compositions and methods for potentiating various antimicrobials and/or minimizing their side-effects. In particular, the present invention relates to pharmaceutical compositions comprising combinations of antimicrobials and cannabinoids, and optionally N-acylethanolamines, and use thereof in treating and/or preventing microbe biofilm formation and microbe-induced pathologies.

BACKGROUND AND SUMMARY

An antimicrobial is an agent that kills microorganisms or inhibits their growth. Antimicrobial medicines can be grouped according to the microorganisms they act primarily against. For example, antibiotics are used against bacteria and antifungals are used against fungi.

Antibiotics, also called antibacterial agents, are a type of antimicrobial drug used in the treatment and prevention of bacterial infection. They may either kill or inhibit the growth of bacteria. Although there are a number of different types of antibiotics, they all work in one of two ways. A bactericidal antibiotic kills the bacteria (for example: penicillin). A bacteriostatic agent stops bacteria from multiplying. Since each type of antibiotics only works against certain types of bacteria or parasites, different antibiotics are used to treat different types of infection.

Antibiotics revolutionized medicine in the 20th century and have (together with vaccination) effectively eradicated diseases such as tuberculosis in the developed world. Their abundances and effectiveness led to overuse, prompting bacteria to develop resistance to certain antibiotics and in certain cases to multi-drug resistance (MDR). This has led to widespread problems with antimicrobial and antibiotic resistance, so much as to prompt the World Health Organization (WHO) to classify antimicrobial resistance as a "serious threat". In 2009, the European Centre for Disease Prevention and Control (ECDC) reported that an estimated 25,000 people die each year in the European Union from antibiotic-resistant bacterial infections (ECDC/EMEA Joint Technical Report, "The bacterial challenge: time to react", published Sep. 17, 2009).

In addition, certain antibiotics have been associated with a range of adverse side effects. Side-effects range from mild to acute, depending on the antibiotics used, the microbial organisms targeted, and the individual patient. Such side effects may reflect the pharmacological or toxicological properties of the antibiotic or may involve hypersensitivity reactions or anaphylaxis. Adverse effects range from fever and nausea to major allergic reactions, including photodermatitis and anaphylaxis. For example, a common side-effect is diarrhea, resulting from disruption of the species composition in the intestinal flora, resulting, for example, in overgrowth of pathogenic bacteria, such as *Clostridium difficile*. Anti-bacterial agents can also affect the vaginal flora and may lead to overgrowth of yeast species of the genus *Candida* in the vulvo-vaginal area. Additional side-effects can result from interaction with other drugs, such as elevated risk of tendon damage from administration of a quinolone antibiotic with a systemic corticosteroid. Furthermore, exposure to antibiotics early in life is associated with increased body mass in humans and mouse models (Katrina Ray, Nature Reviews Endocrinology, 201, Vol. 28, page 623).

In addition, some bacteria form pathogenic structures called biofilms. A biofilm is any group of microorganisms in which cells stick to each other, and often these cells adhere to a living or non-living surface. These adherent cells are frequently embedded within a self-produced matrix of extracellular polymeric substance (EPS). Biofilm extracellular polymeric substance is a polymeric conglomeration generally composed of extracellular DNA, proteins, and oligosaccharides. Microbes form a biofilm in response to many factors, which may include cellular recognition of specific or non-specific attachment sites on a surface, nutritional cues, or in some cases, by exposure of cells to sub-inhibitory concentrations of antibiotics. When a cell switches to the biofilm mode of growth, it undergoes a phenotypic shift in behavior in which large suites of genes are differentially regulated.

Biofilms have been found to be involved in a wide variety of microbial infections in the body, by one estimate 80% of all infections (Biel M A, Methods Mol. Biol, 2010, Vol. 635, pages 175-194). Infectious processes in which biofilms have been implicated include bacterial vaginosis, urinary tract infections, catheter infections, middle-ear infections, formation of dental plaque, gingivitis, coating contact lenses, and more lethal processes such as endocarditis, infections in cystic fibrosis, and infections of permanent indwelling devices such as joint prostheses and heart valves. More recently it has been noted that bacterial biofilms may impair cutaneous wound healing and reduce topical antibacterial efficiency in healing or treating infected skin wounds. Early detection of biofilms in wounds is crucial to successful chronic wound management. Although many techniques have developed to identify bacteria in viable wounds, few have been able to quickly and accurately identify bacterial biofilms.

The main problem with biofilm formation is that it allows the cells inside the biofilm to become more resistant to the body's natural antimicrobials as well as the antibiotics administered in a standard fashion. In fact, depending on the organism and type of antimicrobial and experimental system, biofilm bacteria can be up to a thousand times more resistant to antimicrobial stress than free-swimming bacteria of the same species. Examples of bacteria capable of producing biofilm include *Pseudomonas aeruginosa, Legionella*, Staphylococci, Streptococci and *Candida. S. pneumoniae* is the main cause of community-acquired pneumonia and meningitis in children and the elderly, and of septicemia in HIV-infected persons. *Legionella* bacteria are known to grow under certain conditions in biofilms, in which they are protected against disinfectants.

*Cannabis* is a genus of flowering plants from order Rosales, family Cannabaceae, which includes three different species, *Cannabis sativa, Cannabis* indica and *Cannabis ruderalis*, which are indigenous to Central and South Asia. *Cannabis* has long been used for hemp fiber, for seed and seed oils, for medicinal purposes, and well as being a recreational drug. Pharmacologically, *Cannabis* contains 483 known chemical compounds, including at least 85 different cannabinoids. Cannabinoids, terpenoids, and other compounds are secreted by glandular trichomes that occur most abundantly on the floral calyxes and bracts of female plants.

Cannabinoids are a class of diverse chemical compounds that act on cannabinoid receptors on cells that repress neurotransmitter release in the brain. Cannabinoid receptors are of a class of cell membrane receptors under the G protein-coupled receptor superfamily. As is typical of G protein-coupled receptors, the cannabinoid receptors contain seven transmembrane spanning domains. There are currently two known subtypes of cannabinoid receptors, termed CB1 and CB2, with mounting evidence of more. The CB1 receptor is expressed mainly in the brain (central nervous system), but also in the lungs, liver and kidneys. The CB2 receptor is expressed mainly in the immune system and in hematopoietic cells.

The classical cannabinoids are derived from their respective 2-carboxylic acids (2-GOOH) by decarboxylation, catalyzed by heat, light, or alkaline conditions. Phytocannabinoids (those derived from the *Cannabis* plant) include but not limited to: tetrahydrocannabinol (THC), tetrahydrocannabinolic acid (THCA), cannabidiol (CBD), cannabinol (CBN), cannabigerol (CBG), cannabichromene (CBC), cannabicyclol (CBL), cannabivarin (CBV), tetrahydrocannabivarin (THCV), cannabidivarin (CBDV), cannabichromevarin (CBCV), cannabigerovarin (CBGV) and cannabigerol monomethyl ether (CBGM).

The most notable cannabinoid is the phytocannabinoid A9-tetrahydrocannabinol (THC), which is the primary psychoactive component of the *cannabis* plant. THC has approximately equal affinity for the CBI and CB2 receptors, and it possess activities as a psychoactive agent, analgesic, muscle relaxant, antispasmodic, bronchodilator, neuroprotective, antioxidant and antipruritic agent. Dronabinol is the International Nonproprietary Name (INN) for a pure isomer of THC, (−)-trans-A9-tetrahydrocannabinol. Synthesized dronabinol is marketed as MARINOL (a registered trademark of Solvay Pharmaceuticals). In the United States, MARINOL® is a Schedule III drug, available by prescription, considered to be non-narcotic and to have a low risk of physical or mental dependence. MARINOL® has been approved by the U.S. Food and Drug Administration (FDA) in the treatment of anorexia in AIDS patients, as well as for refractory nausea and vomiting of patients undergoing chemotherapy. An analog of dronabinol, Nabilone (a Schedule II drug), with therapeutic use as an antiemetic and as an adjunct analgesic for neuropathic pain, is available commercially in Canada under the trade name CESAMET®. CESAMET® has also received FDA approval and began marketing in the U.S. in 2006.

Cannabidiol (CBD) is another major phyto-cannabinoid, accounting for up to 40% of the plant's extract in selected cultivars. CBD is considered to have a wider scope of medical applications than THC. An orally-administered liquid containing CBD has received orphan drug status in the US, for use as a treatment for Dravet syndrome, under the trade name EPIDIOLEX®. Anandamide (N-arachidonoylethanolamine, AEA), one of the major components of endocannabinoid system, is a THC mimetic. Its effects can be either central, in the brain, or peripheral, in other parts of the body and are mediated primarily by CB1 in the central nervous system, and CB2 in the periphery. However, short half-life due to the action of the enzyme fatty acid amide hydrolase (FAAH), presents a disadvantage for potential therapeutic use. N-acylethanolamines (NAEs) are lipid-derived signaling molecules. They are formed when one of several types of acyl group is linked to the nitrogen atom of ethanolamine.

Methods for synthesizing N-acylethanolamine compounds are well known in the art. As described in Lambert et al (Lambert D M, Vandevoorde S, Jonson K O, Fowler C J., Curr. Med. Chem., 2002; 9:663-74; U.S. Pat. No. 5,506,224 and United States patent application 2005/0054730), Palmitoylethanolamide (PEA) was initially synthesized by refluxing ethanolamine with palmitic acid, yielding white crystals melting at 98-99° C.

Palmitoylethanolamide (PEA, also known as N-(2-hydroxyethyl) hexadecanamide; Hydroxyethyl-palmitamide; palmidrol; and N-palmitoylethanolamine) is an endogenous fatty acid amide, belonging to the class of nuclear factor agonists. PEA has been demonstrated to bind to a receptor in the cell-nucleus (a nuclear receptor) and exerts a variety of biological functions related to chronic pain and inflammation. Studies have shown that PEA interacts with distinct non-CB1/CB2 receptors, suggesting that PEA utilizes a unique "parallel" endocannabinoid signaling system. PEA has been shown to have anti-inflammatory, anti-nociceptive, neuroprotective, and anti-convulsant properties. PEA has also been shown to possess anti-craving effects in *cannabis* dependent patients, is efficacious in the treatment of withdrawal symptoms, produces a reduction of *cannabis* consumption and is effective in the prevention of *cannabis* induced neurotoxicity and neuro-psychiatric disorders.

Described in 1998 by Mechoulam and co-workers (Ben-Shabat et al. Eur. J. Pharmacol., 1998, Vol. 353(1), pages 23-31), the basic idea of the "entourage effect" is that cannabinoids within the *cannabis* plant work together, or possess synergy, and affect the body in a mechanism similar to the body's own endocannabinoid system.

This theory serves as the foundation for a somewhat controversial idea within pharmacology, that in certain cases whole plant extractions serve as better therapeutic agents than individual cannabinoid extractions. The entourage effect theory has been expanded in recent times by Wagner and Ulrich-Merzenich (Wagner et al., Phytomedicine, 2009, Vol. 16(2-3), pages 97-110), who define the four basic mechanisms of whole plant extract synergy as follows: (a) ability to affect multiple targets within the body, (b) ability to improve the absorption of active ingredients, (c) ability to overcome bacterial defense mechanisms, and (d) ability to minimize adverse side effects.

PEA, beside its proposed "entourage effect" on cannabinoids such as THC, possesses its own antimicrobial properties. Already in 1960s, the protective effects of PEA from egg yolk in Streptococcal Infections were noticed (Keppel Hesselink J M, Int. J. Inflam., 2013). PEA exerts protective effects and increases the resistance against infections by stimulation of phagocytosis of *Escherichia coli* KI by macrophages (Redlich S, J. Neuroinflammation. 2014 Jun. 14).

There are currently considerable challenges with the treatment of infections caused by strains of clinically relevant bacteria that show multi-drug-resistance (MDR), such as methicillin-resistant *Staphylococcus aureus* (MRSA) and the recently emerged and extremely drug-resistant *Mycobacterium tuberculosis* XDR-TB. New anti-bacterial agents are therefore urgently needed, but only one new class of antibacterial has been introduced in the last 30 years.

There remains a need in the field of antimicrobial therapy for pharmaceutical combinations of antimicrobial agents with cannabinoids and other agents capable of increasing the potency of the antimicrobial agents, decreasing the minimal therapeutic dosages of the antimicrobial agents, thus minimizing the development of drug resistance, reducing antimicrobial-associated side effects, preventing biofilm formation and/or treating the established biofilms, particularly in humans.

SUMMARY OF THE INVENTION

The present invention relates to compositions comprising antimicrobials and cannabinoids and optionally N-acylethanolamines, with enhanced anti-microbial therapeutic efficacy and/or reduced anti-microbial-related side effects. The present invention further relates to methods for the use of these compositions in treating diseases or conditions for which anti-microbial treatment is prescribed.

The present invention is based in part on surprising experimental findings that combinations of anti-microbial agents with cannabinoids enhance the anti-microbial activity of the anti-microbial agents. As is exemplified herein below the efficacy of the combinations of antibiotics and cannabinoids is synergistic. It has further been surprisingly found that N-acylethanolamines further increase this effect.

The present invention provides, in one aspect, a synergistic pharmaceutical composition comprising at least one anti-bacterial agent, at least one cannabinoid, and a pharmaceutically acceptable carrier.

In certain embodiments, the anti-bacterial efficacy of the pharmaceutical composition is similar to, or better than, the anti-bacterial efficacy of the same pharmaceutical composition comprising 2 to 150 times the amount of the anti-bacterial agent without the cannabinoid.

In certain embodiments, the weight ratio between the anti-bacterial agent(s) and the cannabinoid(s) is between about 1000:1 to 1:1000, respectively. In certain embodiments, the weight ratio between the anti-bacterial agent(s) and the cannabinoid(s) is between about 500:1 to 1:100, respectively. In certain embodiments, the weight ratio between the anti-bacterial agent(s) and the cannabinoid(s) is between about 300:1 to 1:100, respectively. In certain embodiments, the weight ratio between the anti-bacterial agent(s) and the cannabinoid(s) is between about 250:1 to 1:50, respectively In certain embodiments, the weight ratio between the anti-bacterialagent(s) and the cannabinoid(s) is between about 10:1 to 1:10, respectively In certain embodiments, the weight ratio between the anti-bacterial agent(s) and the cannabinoid(s) is between about 2:10 to 3:200, respectively. In certain embodiments, the weight ratio between the anti-bacterial agent(s) and the cannabinoid(s) is between about 130:1 to 20:1, respectively. In certain embodiments, the weight ratio between the anti-bacterial agent(s) and the cannabinoid(s) is between about 100:1 to 500:1, respectively. In certain embodiments, the weight ratio between the anti-bacterial agent(s) and the cannabinoid(s) is between about 1:1 to 1:10, respectively. In certain embodiments, the weight ratio between the anti-bacterial agent(s) and the cannabinoid(s) is between about 1:5 to 1:20, respectively.

In certain embodiments, the weight ratio between the anti-bacterial agent(s) and the cannabinoid(s) is between about 5:1 to 1:5, respectively. In certain embodiments, the weight ratio between the anti-bacterial agent(s) and the cannabinoid(s) is between about 2:5 to 3:100, respectively. In certain embodiments, the weight ratio between the anti-bacterial agent(s) and the cannabinoid(s) is between about 65:1 to 10:1, respectively. In certain embodiments, the weight ratio between the anti-bacterial agent(s) and the cannabinoid(s) is about 250:1, respectively. In certain embodiments, the weight ratio between the anti-bacterial agent(s) and the cannabinoid(s) is about 1:5, respectively. In certain embodiments, the weight ratio between the anti-bacterial agent(s) and the cannabinoid(s) is about 1:10, respectively.

In certain embodiments, the weight ratio between gentamicin and THC is between about 5:1 to 1:5, respectively. In certain embodiments, the weight ratio between gentamicin and THC is between about 2:5 to 3:100, respectively. In certain embodiments, the weight ratio between gentamicin and THC is between about 65:1 to 10:1, respectively. In certain embodiments, the weight ratio between ampicillin and THC is about 250:1, respectively. In certain embodiments, the weight ratio between carbenicillin and THC is about 1:5, respectively. In certain embodiments, the weight ratio between gentamicin and THC is about 1:10, respectively.

In certain embodiments, at least one anti-bacterial agent is selected from the group consisting of an aminoglycoside, a penicillin, a cephalosporin, a tetracycline, a macrolide, a clindamycin, a sulfonamide, a metronidazole, a quinolone, a derivative thereof, a salt thereof and any combination thereof.

In certain embodiments, the at least one anti-bacterial agent is an aminoglycoside or a salt thereof. In certain embodiments, the aminoglycoside is gentamicin or a salt thereof. In certain embodiments, the anti-bacterial efficacy of the pharmaceutical composition is similar to, or better than, the anti-bacterial efficacy of the same pharmaceutical composition comprising 2 to 64 times the amount of the anti-bacterial agent without the cannabinoid. In certain embodiments, the anti-bacterial efficacy is determined against gentamicin-sensitive bacteria. In certain embodiments, gentamicin-sensitive bacteria are selected from the group consisting of non-resistant *Staphylococcus aureus* and methicillin-resistant *Staphylococcus aureus* (MRSA).

In certain embodiments, the at least one anti-bacterial agent is a penicillin or a salt thereof. In certain embodiments, the penicillin is ampicillin or a salt thereof. In certain embodiments, the anti-bacterial efficacy of the pharmaceutical composition is similar to, or better than, the anti-bacterial efficacy of the same pharmaceutical composition comprising 2 to 16 times the amount of the anti-bacterial agent without the cannabinoid. In certain embodiments, the anti-bacterial efficacy is determined against ampicillin resistant bacteria. In certain embodiments, the ampicillin-resistant bacteriaare methicillin-resistant *Staphylococcus aureus* (MRSA). In certain embodiments, the penicillin is carbenicillin or a salt thereof. In certain embodiments, the anti-bacterial efficacy of the pharmaceutical composition is similar to, or better than, the anti-bacterial efficacy of the same pharmaceutical composition comprising 2 to 16 times the amount of the anti-bacterial agent without the cannabinoid. In certain embodiments, the anti-bacterial efficacy is determined against *Streptococcus pneumoniae*.

In certain embodiments, the at least one cannabinoid is selected from tetrahydrocannabinol (THC), tetrahydrocannabinolic acid (THCA), cannabidiol (CBD), cannabinol (CBN), cannabigerol (CBG), cannabichromene (CBC), cannabicyclol (CBL), cannabivarin (CBV), tetrahydrocannabivarin (THCV), cannabidivarin (CBDV), cannabichromevarin (CBCV), cannabigerovarin (CBGV), cannabigerol monomethyl ether (CBGM), derivatives thereof, salts thereof and any combination thereof.

In certain embodiments, the cannabinoid is THC or a salt thereof. In certain embodiments, the cannabinoid is CBD or a salt thereof. In certain embodiments, the cannabinoid comprises a mixture of THC or a salt thereof and CBD or a salt thereof.

In certain embodiments, the pharmaceutical composition described above further comprises at least one N-acylethanolamine. In certain embodiments, the N-acylethanolamine is selected from the group consisting of N-palmitoylethanolamine (PEA), Me-palmitoylethanolamide (Me-PEA), palmitoylcyclohexamide, palmitoylbutylamide, palmitoylisopropylamide, oleoylethanolamine (OEA), palmitoylisopropylamide (PIA), derivatives thereof, salts thereof and any combination thereof. In certain embodiments, the N-acylethanolamine is PEA or a salt thereof.

In certain embodiments, the anti-bacterial efficacy of the pharmaceutical composition and the same pharmaceutical composition without the cannabinoid are determined against the same bacteria, selected from the group consisting of gentamicin-sensitive *Staphylococcus aureus* ATCC strain 25923, methicillin-resistant *Staphylococcus aureus* and *Streptococcus pneumoniae*.

In certain embodiments, the pharmaceutically acceptable carrier is suitable for a route of administration selected from the group consisting of oral, topical, mucosal, nasal, rectal, sublingual, parenteral, intravenous, intramuscular, and subcutaneous administration.

The present invention further provides, in another aspect, a pharmaceutical composition as described above, for use in treating or preventing a bacterial infection or bacterial biofilm.

In certain embodiments, the use creates or extends the susceptibility of the bacteria to the anti-bacterial agent compared to the susceptibility of the bacteria to the anti-bacterial agent without the at least one cannabinoid. In certain embodiments, the use is associated with a reduced side effect compared to the use of the at least one anti-bacterial agent without the at least one cannabinoid. In certain embodiments, the side effect is selected from the group consisting of hypersensitivity towards the at least one anti-bacterial agent, an allergic reaction to the at least one anti-bacterial agent, fever, nausea, diarrhea and any combination thereof. In certain embodiments, the use is associated with increased anti-bacterial activity compared to the use of the at least one anti-bacterial agent without the at least one cannabinoid. In certain embodiments, the use is associated with a reduced dosage of the at least one anti-bacterial agent compared to the use of the at least one anti-bacterial agent without the at least one cannabinoid. In certain embodiments, the use is associated with an expended therapeutic window of the at least one anti-bacterial agent compared to the use of the at least one anti-bacterial agent without the at least one cannabinoid.

In certain embodiments, the bacterial infection or the bacterial biofilm is selected from the group consisting of a *Staphylococcus* spp. infection or, *Pseudomonas aeruginosa* infection or biofilm, *Porphyromonas* spp. infection or biofilm, *Moraxella* spp. infection or biofilm, *Peptostreptococcus* spp. infection or biofilm, *Enterococcus* spp. infection or biofilm, *Escherichia coli* infection or biofilm, *Klebsiella* infection or biofilm, Streptococcal infection or biofilm, *Treponema pallidum* subspecies *pallidum* infection or biofilm, and *Borrelia* infection or biofilm.

The present invention further provides, in another aspect, a method of treating or preventing a bacterial infection or a bacterial biofilm in a subject in need thereof, the method comprising the step of administering to the subject a combination of a first pharmaceutical composition comprising at least one anti-bacterial agent and a second pharmaceutical composition comprising at least one cannabinoid.

In certain embodiments, the method described above further comprises the step of administering to the subject a pharmaceutical composition comprising at least one N-acylethanolamine.

In certain embodiments, route of administration is selected from the group consisting of oral, topical, mucosal, nasal, rectal, sublingual, parenteral, intravenous, intramuscular and subcutaneous administering. In certain embodiments, an aminoglycoside is administered intravenously, intramuscularly, topically, orally or in a nebulized form. In certain embodiments, penicillin is administered intravenously, parenterally or orally. In certain embodiments, the at least one anti-bacterial agent is administered together with the at least one cannabinoid. In certain embodiments, the at least one anti-bacterial agent is administered separately from the at least one cannabinoid. In certain embodiments, the subject is a human.

The present invention further provides, in another aspect, a kit comprising (a) a first pharmaceutical composition comprising at least one anti-bacterial agent and (b) a second pharmaceutical composition comprising at least one cannabinoid.

In certain embodiments, the kit described above further comprises a third pharmaceutical composition comprising at least one N-acylethanolamine.

In certain embodiments, the kit is for use in treating or preventing a bacterial infection or a bacterial biofilm.

The present invention further provides, in another aspect, a method of enhancing the efficacy of an anti-bacterial agent in a patient in need of anti-bacterial treatment, comprising co-administering at least one anti-bacterial agent and at least one cannabinoid to the patient.

In certain embodiments, an aminoglycoside is administered intravenously, intramuscularly, topically, orally or in a nebulized form. In certain embodiments, penicillin is administered intravenously, intramuscularly or orally. In certain embodiments, the at least one anti-bacterial agent and the at least one cannabinoid are administered separately. In certain embodiments, the at least one anti-bacterial agent and the at least one cannabinoid are administered together. In certain embodiments, the patient is a human.

Other objects, features and advantages of the present invention will become clear from the following description.

BRIEF DESCRIPTION OF THE DRAWINGS

FIG. 2 is a spreadsheet representation of the OD value results of the indicated treatments in Example 2.

FIG. 3 is a spreadsheet representation of the OD value results of the indicated treatments in Example 3.

FIG. 4 is a spreadsheet representation of the OD value results of the indicated treatments in Example 4.

FIG. 5 is a spreadsheet representation of the OD value results of the indicated treatments in Example 5.

FIG. 6 is a spreadsheet representation of the OD value results of the indicated treatments in Example 6.

FIG. 7 is a spreadsheet representation of the OD value results of the indicated treatments in Example 10.

DETAILED DESCRIPTION OF THE INVENTION

Figure 1:
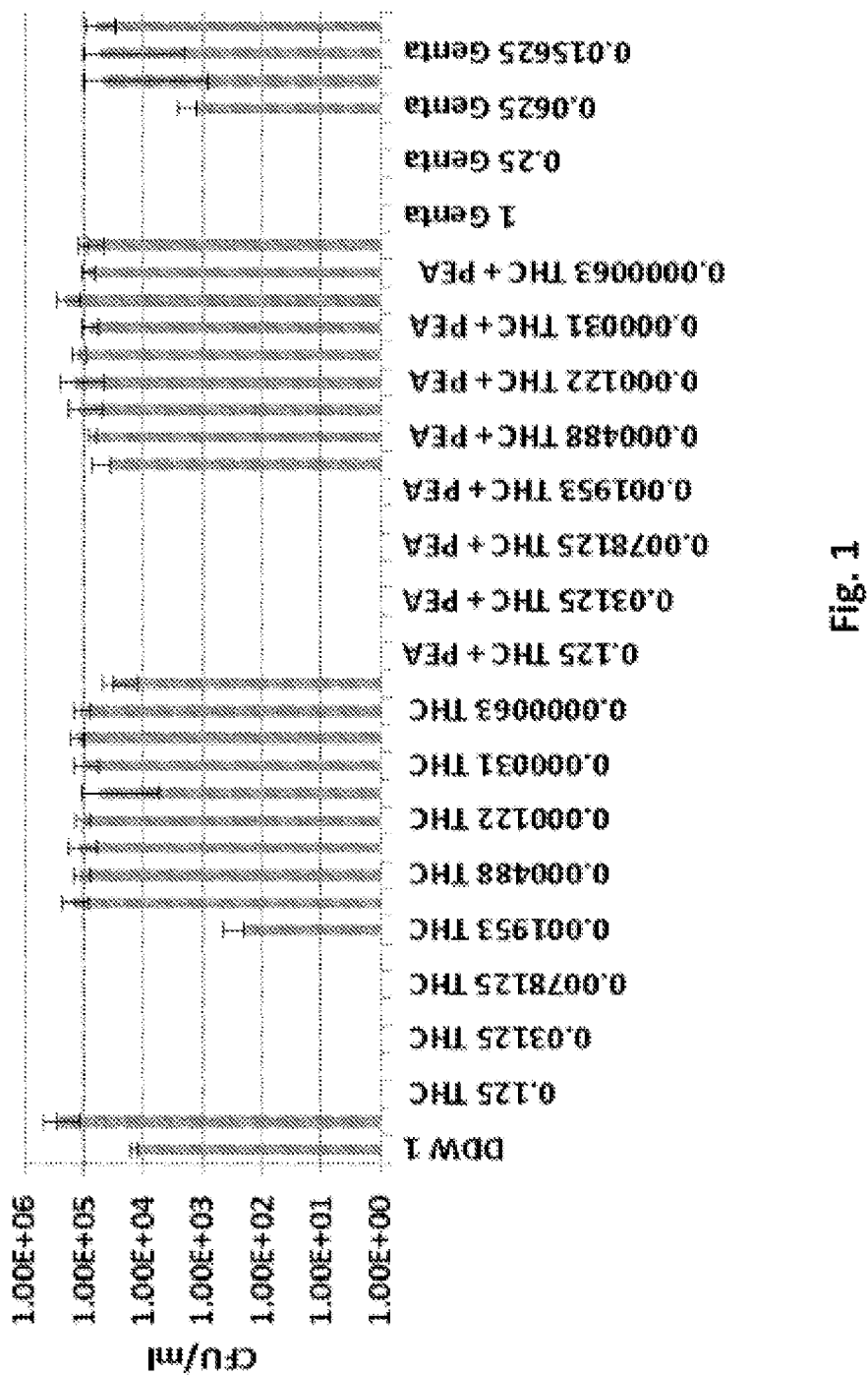
FIG. 1 is a bar graph representing C.F.U/mL concentration results of the indicated treatments in Example 1.

The present invention relates to combinations comprising an antimicrobial agent and a cannabinoid. The present invention further relates to combinations comprising an antimicrobial agent, a cannabinoid and an N-acylethanolamine. The present invention further relates to methods for the use of these compositions in treating microbial-related infectious diseases or conditions that are amenable to treatment with antimicrobial agents.

For example, pharmaceutical or veterinary compositions according to the invention can be used to treat clinically-relevant bacteria that show multidrug-resistance (MDR), such as methicillin-resistant *Staphylococcus aureus* (MRSA) and the extremely drug-resistant *Mycobacterium tuberculosis* XDR-TB, for which antibiotics exhibit limited efficacy. Moreover, these compositions may be useful in preventing the formation of a biofilm or contributing to the disintegration of an established biofilm structure, thus treating said condition.

Bacterial and fungi infections are routinely treated with antimicrobial agents, a therapy frequently accompanied by various side effects, which may reflect the pharmacological or toxicological properties of the antimicrobial agents. These side effects often range from fever and nausea to major allergic reactions, including photo-dermatitis and anaphylaxis. Thus, there is a great need to decrease the dosages of antimicrobial agents in treatment, prolong and/or potentiate their therapeutic effect, and/or reduce their associated side effects.

The pharmaceutical and veterinary compositions of the invention provide improved medicaments compared to current therapies, exhibiting an increased therapeutic activity, while minimizing the dosages of antimicrobial agents administered and reducing associated adverse events.

The present invention provides, in one aspect, a composition comprising at least one anti-microbial agent, at least one cannabinoid, and an acceptable carrier.

As used herein, the term "anti-microbial agent" is used to encompass materials, typically chemicals, which kill microbes or retard the growth of microbes to a statistically significant degree. The term "anti-microbial agent" should be understood to include bactericides, fungicides, and other such agents. The terms "anti-microbial", "bactericide" and "fungicide" are well-known to those skilled in the art and their meanings will be readily discerned by the context in which each term is used.

The present invention discloses that cannabinoid compounds, with or without N-acylethanolamine, exhibit an antimicrobial agents-sparing effect. The term "antimicrobial agent-sparing" or "antimicrobial-sparing" as used herein refers to the enablement of the use of low dosages of antimicrobial agents in instances wherein a mid- or high-dosages of antimicrobial agents are typically required. The cannabinoid and N-acylethanolamine compounds according to the present invention include pharmaceutically acceptable forms thereof, including isomers such as diastereomers and enantiomers, salts, solvates, and polymorphs, as well as racemic mixtures.

The term "cannabinoid" as used herein generally refers to a class of diverse chemical compounds that act on cannabinoid receptors on cells that repress neurotransmitter release in the brain. Ligands for these receptor proteins include the endocannabinoids (produced naturally in the body by humans and animals), the phytocannabinoids (found in *cannabis* and some other plants), and synthetic cannabinoids (manufactured artificially). There are at least 85 different cannabinoids isolated from *cannabis*, exhibiting varied effects (El-Alfy et al., Pharmacology Biochemistry and Behavior, 2010, Vol. 95(4), pages 434^142).

In certain embodiments, the weight ratio between the anti-bacterial agent(s) and the cannabinoid(s) is between about 1000:1 to 1:1000, respectively. In certain embodiments, the weight ratio between the anti-bacterial agent(s) and the cannabinoid(s) is between about 500:1 to 1:100, respectively. In certain embodiments, the weight ratio between the anti-bacterial agent(s) and the cannabinoid(s) is between about 300:1 to 1:100, respectively. In certain embodiments, the weight ratio between the anti-bacterial agent(s) and the cannabinoid(s) is between about 250:1 to 1:50, respectively. In certain embodiments, the weight ratio between the anti-bacterial agent(s) and the cannabinoid(s) is between about 10:1 to 1:10, respectively. In certain embodiments, the weight ratio between the anti-bacterial agent(s) and the cannabinoid(s) is between about 2:10 to 3:200, respectively. In certain embodiments, the weight ratio between the anti-bacterial agent(s) and the cannabinoid(s) is between about 130:1 to 20:1, respectively. In certain embodiments, the weight ratio between the anti-bacterial agent(s) and the cannabinoid(s) is between about 100:1 to 500:1, respectively. In certain embodiments, the weight ratio between the anti-bacterial agent(s) and the cannabinoid(s) is between about 1:1 to 1:10, respectively. In certain embodiments, the weight ratio between the anti-bacterial agent(s) and the cannabinoid(s) is between about 1:5 to 1:20, respectively.

In certain embodiments, the weight ratio between the anti-bacterial agent(s) and the cannabinoid(s) is between about 5:1 to 1:5, respectively. In certain embodiments, the weight ratio between the anti-bacterial agent(s) and the cannabinoid(s) is between about 2:5 to 3:100, respectively. In certain embodiments, the weight ratio between the anti-bacterial agent(s) and the cannabinoid(s) is between about 65:1 to 10:1, respectively. In certain embodiments, the weight ratio between the anti-bacterial agent(s) and the cannabinoid(s) is about 250:1, respectively. In certain embodiments, the weight ratio between the anti-bacterial agent(s) and the cannabinoid(s) is about 1:5, respectively. In certain embodiments, the weight ratio between the anti-bacterial agent(s) and the cannabinoid(s) is about 1:10, respectively.

In certain embodiments, the weight ratio between gentamicin and THC is between about 5:1 to 1:5, respectively. In certain embodiments, the weight ratio between gentamicin and THC is between about 2:5 to 3:100, respectively. In certain embodiments, the weight ratio between gentamicin and THC is between about 65:1 to 10:1, respectively. In certain embodiments, the weight ratio between ampicillin and THC is about 250:1, respectively. In certain embodiments, the weight ratio between carbenicillin and THC is about 1:5, respectively. In certain embodiments, the weight ratio between gentamicin and THC is about 1:10, respectively.

In certain embodiments, the anti-microbial efficacy of the composition is similar to, or better than, the anti-microbial efficacy of the same pharmaceutical composition comprising 2 to 150 times the amount of the anti-microbial agent without the cannabinoid.

It should be understood that there are many alternative ways to test the anti-microbial or antibacterial efficacy of a composition well within the knowledge of a person of average skill in the art, and that the methods used in the Examples section are only representative methods for testing and determining the anti-microbial efficacy of a composition, e.g. a composition according to the present invention. The term "the same composition" as used herein merely means a corresponding composition which is identical to the original composition with only the stated exception(s).

In certain embodiments, the method of testing the anti-bacterial efficacy of a composition (or any test solution), comprises the following steps: (a) inoculation of bacteria (e.g. from a −80° C. stock) into 3 mL Muller Hinton (MH) medium; (b) incubation of the inoculated medium at 37° C. under agitation of 250 rpm for 18-20 hours, thus obtaining a starter culture; (c) diluting the starter culture using saline to obtain working cultures of $5*10^5$ or $10^6$ bacteria/mL; (d) combining the starter culture and the tested composition in a test container, e.g. a 96-well plate; (e) incubating the test container at 37° C. under shaking (100 rpm) for 18-20 hours; and (f) determining the viability of bacteria in the test container, thus determining the anti-bacterial efficacy of the composition, e.g. via determining the optical density (OD) of the bacterial culture. Routine calibrations and/or modifications of this method are well within the capabilities of any person of average skill in the art.

The term "minimal inhibitory concentration" or "MIC" as used herein relates to the minimal concentration of an agent, or a combination of agents, in which bacteria are substantially killed or at least not substantially grow. The cutoff value to determine the MIC in the experimental section was set to an optical density (OD) value of ≤0.1 after an overnight incubation of the bacteria together with the tested antibacterial agent(s).

In certain embodiments, the composition is a pharmaceutical composition and the carrier is a pharmaceutically-acceptable carrier. In certain embodiments, the composition is a veterinary composition and the carrier is a veterinary-acceptable carrier. In certain embodiments, the composition is a cosmetic composition and the carrier is a cosmetically-acceptable carrier.

As used herein, the term "pharmaceutical composition" refers to a preparation of the active agents described herein with other chemical components such as physiologically suitable carriers and excipients. The purpose of a pharmaceutical composition is to facilitate administration of a compound to an organism. As used herein, the phrase "pharmaceutically acceptable carrier" refers to a carrier, an excipient or a diluent that does not cause significant irritation to an organism and does not abrogate the biological activity and properties of the administered compound. An adjuvant is included under these phrases.

The term "excipient" as used herein refers to an inert substance added to a pharmaceutical composition to further facilitate administration of an active ingredient. Examples of excipients, without limitation, include calcium carbonate, calcium phosphate, various sugars and types of starch, cellulose derivatives, gelatin, vegetable oils, polyethylene glycols and combinations thereof.

The term "carrier" as used herein refers to a diluent, adjuvant, excipient, or vehicle with which the compound is administered. Such pharmaceutical carriers can be sterile liquids, such as water and oils. Water or aqueous solution saline solutions and aqueous dextrose and glycerol solutions may be employed as carriers, particularly for injectable solutions. Suitable pharmaceutical carriers are described in "Remington's Pharmaceutical Sciences" by E. W. Martin, 18th Edition.

Suitable routes of administration may, for example, include oral, topical, rectal, nasal, transmucosal, intestinal, or parenteral delivery, including intramuscular, subcutaneous, and intramedullary injections, as well as intrathecal, direct intraventricular, intravenous, intraperitoneal, intranasal, or intraocular injections. Alternately, one may administer the pharmaceutical composition in a local rather than systemic manner, for example, via injection of the pharmaceutical composition directly into a tissue region of a patient.

The phrase "pharmaceutically acceptable" as used herein refers to molecular entities and compositions that are physiologically tolerable and do not typically produce an allergic or similar toxicity when administered to an individual. The term "pharmaceutically acceptable" may mean approved by a regulatory agency (for example, the U.S. Food and Drug Agency) or listed in a generally recognized pharmacopeia for use in animals (e.g., the U.S. Pharmacopeia).

The term "veterinary composition" encompasses the full range of compositions for internal administration and feeds and drinks which can be consumed by animals. Typical veterinary dosage forms for internal administration are orally administrable dosage forms, such as pastes, solutions, tablets, etc. However, injectable compositions are also envisaged. The compositions of the present invention may also be medicated fodders, feeds, nutriments, premixes, drinking waters and drinking water additives. Typically, for mixing in feed, the composition is provided as a powder and for mixing in drinking water the composition is provided as a fluid.

As used herein, the term "cosmetic composition" means a composition which is intended to be applied onto the consumer's skin, particularly, onto the facial skin or onto the facial skin surrounding the eyes, so as to regulate the condition of the skin and/or to improve the appearance of the skin.

Techniques for formulation and administration of drugs are well known in the art, and may be found, e.g. in "Remington's Pharmaceutical Sciences," Mack Publishing Co., Easton, Pa. Pharmaceutical compositions of the present invention may be manufactured by processes well known in the art, e.g., by means of conventional mixing, dissolving, granulating, dragee-making, levigating, emulsifying, encapsulating, entrapping, or lyophilizing processes. Pharmaceutical compositions for use in accordance with the present invention may be formulated in conventional manner using one or more physiologically acceptable carriers comprising excipients and auxiliaries, which facilitate processing of the active ingredients into preparations that can be used pharmaceutically. Proper formulation is dependent upon the route of administration chosen. For topical, the active ingredients of the pharmaceutical composition may be formulated in cremes, ointments, solutions, patches, sprays, lotions, liniments, varnishes, solid preparations such as silicone sheets, and the like.

In certain embodiments, the composition is not liquid in room temperature. In certain embodiments, the composition is a solid or a semi-solid in room temperature. In certain embodiments, the composition is fully coated by enteric coating.

In certain embodiments, the antibiotic is selected from bactericidal antibiotics and bacteriostatic antibiotics. In certain embodiments, the antibiotic is selected from, but not limited to, antibiotic classes of aminoglycosides, ansamycins, carbacephem, carbapenems, cephalosporins (First generation), cephalosporins (Second generation), cephalosporins (Third generation), cephalosporins (Fourth generation), cephalosporins (Fifth generation), glycopeptides, lincosamides (Bs), lipopeptide, macrolides (Bs), monobactams, nitrofurans, oxazolidinones (Bs), penicillins, penicillin combinations, Polypeptides based antibiotics, quinolones/fluoroquinolones, sulfonamides (Bs), tetracyclines (Bs), and drugs against mycobacteria.

In certain embodiments, the at least one anti-microbial agent is an anti-bacterial agent. In certain embodiments, the at least one anti-bacterial agent is selected from the group consisting of an aminoglycoside, a penicillin, a cephalosporin, a tetracycline, a macrolide, a clindamycin, a sulfonamide, a metronidazole, a quinolone, a derivative thereof, a salt thereof and any combination thereof. Each possibility represents a separate embodiment of the invention.

In certain embodiments, aminoglycosides class of antibiotic lists, among others, the following compounds: Amikacin, gentamicin, Kanamycin, Neomycin, Netilmicin, Tobramycin, Paromomycin and Streptomycin. In certain embodiments, ansamycins class of antibiotics lists, among others, the following compounds: Geldanamycin, Herbimycin and Herbimycin. In certain embodiments, carbacephems class of antibiotics lists, among others, the following compounds: Loracarbef. In certain embodiments, carbapenems class of antibiotics lists, among others, the following compounds: Ertapenem, Doripenem, Imipenem/Cilastatin and Meropenem. In certain embodiments, cephalosporins (First generation) class of antibiotics lists, among others, the following compounds: Cefadroxil, Cefazolin, Cefalotin or Cefalothin and Cefalexin. In certain embodiments, cephalosporins (Second generation) class of antibiotics lists, among others, the following compounds: Cefaclor, Cefamandole, Cefoxitin, Cefprozil and Cefuroxime. In certain embodiments, cephalosporins (Third generation) class of antibiotics lists, among others, the following compounds: Cefixime, Cefdinir, Cefditoren, Cefoperazone, Cefotaxime, Cefpodoxime, Ceftazidime, Ceftibuten, Ceftizoxime and Ceftriaxone. In certain embodiments, cephalosporins (Fourth generation) class of antibiotics lists, among others, the following compounds: Cefepime. In certain embodiments, cephalosporins (Fifth generation) class of antibiotics lists, among others, the following compounds: Ceftaroline fosamil and Ceftobiprole. In certain embodiments, glycopeptides class of antibiotics lists, among others, the following compounds: Teicoplanin, Vancomycin, Telavancin, Dalbavancin and Oritavancin. In certain embodiments, lincosamides (Bs) class of antibiotics lists, among others, the following compounds: Clindamycin and Lincomycin. In certain embodiments, lipopeptide class of antibiotics lists, among others, the following compound: Daptomycin. In certain embodiments, macrolides (Bs) class of antibiotics lists, among others, the following compounds: Azithromycin, Clarithromycin, Dirithromycin, Erythromycin, Roxithromycin, Troleandomycin, Telithromycin and Spiramycin. In certain embodiments, monobactams class of antibiotics lists, among others, the following compound: Aztreonam. In certain embodiments, nitrofurans class of antibiotics lists, among others, the following compounds: Furazolidone and Nitrofurantoin (Bs). In certain embodiments, oxazolidinones (Bs) class of antibiotics lists, among others, the following compounds: Linezolid, Posizolid, Radezolid and Torezolid. In certain embodiments, penicillin class of antibiotics and combinations thereof lists, among others, the following compounds: Amoxicillin, Ampicillin, Azlocillin, Carbenicillin, Cloxacillin, Dicloxacillin, Dicloxacillin, Mezlocillin, Methicillin, Nafcillin, Oxacillin, Penicillin G, Penicillin V, Piperacillin, Temocillin and TicarciUin. In certain embodiments, Polypeptides class of antibiotics lists, among others, the following compounds: Bacitracin, Colistin and Polymyxin B. In certain embodiments, quinolones/fluoroquinolone class of antibiotics lists, among others, the following compounds: Ciprofloxacin, Enoxacin, Gatifloxacin, Gemifloxacin, Levofloxacin, Lomefioxacin, Moxifloxacin, Nalidixic acid, Norfloxacin, Ofloxacin, Trovafloxacin, Grepafloxacin, Sparfloxacin and Temafloxacin. In certain embodiments, sulfonamides (Bs) class of antibiotics lists, among others, the following compounds: Mafenide, Sulfacetamide, Sulfadiazine, Sulfadiazine, Sulfadimethoxine, Sulfamethizole, Sulfamethoxazolem, Sulfanilimide (archaic), Sulfasalazine, Sulfisoxazole, TrimethoprimSulfamethoxazole and Sulfonamidochrysoidine (archaic). In certain embodiments, the tetracyclines (Bs) class of antibiotics lists, among others, the following compounds: Demeclocycline, Doxycycline, Minocycline, Oxytetracycline and Tetracycline. In certain embodiments, antibiotics against mycobacteria include, among others, the following compounds: Clofazimine, Dapsone, Capreomycin, Cycloserine, Ethambutol (Bs), Ethionamide, Isoniazid, Pyrazinamide, Rifampicin, Rifabutin, Rifapentine and Streptomycin. In certain embodiments, unclassified antibiotics include, among others, the following compounds: Arsphenamine, Chloramphenicol (Bs), Fosfomycin, Fusidic acid, Metronidazole, Mupirocin, Platensimycin, Quinupristin/Dalfopristin, Thiamphenicol, Tigecycline (Bs), Tinidazole and Trimethoprim (Bs).

The term "antibiotic" or "antibacterial" as used herein generally refers to any compound which kills, stops the progression or delays the progression of bacteria. These terms further encompass a class of diverse chemical compounds that either target the bacterial cell wall (penicillins and cephalosporins) or the cell membrane (polymyxins), or interfere with essential bacterial enzymes (rifamycins, lipiarmycins, quinolones, and sulfonamides), have bactericidal activities, or abrogate protein synthesis (macrolides, lincosamides and tetracyclines), known as "Bacteriostatics" (with the exception of bactericidal aminoglycosides). Further categorization is based on their target specificity. "Narrow-spectrum" antibacterial antibiotics target specific types of bacteria, such as Gram-negative or Gram-positive bacteria, whereas "broad-spectrum" antibiotics affect a wide range of bacteria.

In certain embodiments, the at least one anti-bacterial agent is an aminoglycoside or a salt thereof. In certain embodiments, the aminoglycoside is gentamicin or a salt thereof. In certain embodiments, the anti-microbial efficacy of the pharmaceutical composition is similar to, or better than, the anti-microbial efficacy of the same pharmaceutical composition comprising 2, 4, 8, 16, 32 or 64 times the amount of the anti-microbial agent without the cannabinoid. In certain embodiments, the anti-microbial efficacy is determined against gentamicin-sensitive bacteria. In certain embodiments, the gentamicin-sensitive bacteria are selected from the group consisting of non-resistant *Staphylococcus aureus* and methicillin-resistant *Staphylococcus aureus* (MRSA). Each possibility represents a separate embodiment of the invention.

In certain embodiments, the at least one anti-bacterial agent is a penicillin or a salt thereof. In certain embodiments, the penicillin is ampicillin or a salt thereof. In certain embodiments, the anti-microbial efficacy of the pharmaceutical composition is similar to, or better than, the anti-microbial efficacy of the same pharmaceutical composition comprising 2, 4, 8 or 16 times the amount of the anti-microbial agent without the cannabinoid. In certain embodiments, the anti-microbial efficacy is determined against ampicillin-resistant bacteria. In certain embodiments, the ampicillin-resistant bacteria are methicillin-resistant *Staphylococcus aureus* (MRSA). In certain embodiments, the penicillin is carbenicillin or a salt thereof. In certain embodiments, the anti-microbial efficacy of the pharmaceutical composition is similar to, or better than, the anti-microbial efficacy of the same pharmaceutical composition comprising 2 or 4 times the amount of the anti-microbial agent without the cannabinoid. In certain embodiments, the anti-microbial efficacy is determined against *Streptococcus pneumoniae*.

In certain embodiments, the at least one cannabinoid is selected from tetrahydrocannabinol (THC), tetrahydrocannabinolic acid (THCA), cannabidiol (CBD), cannabinol (CBN), cannabigerol (CBG), cannabichromene (CBC), cannabicyclol (CBL), cannabivarin (CBV), tetrahydrocannabivarin (THCV), cannabidivarin (CBDV), cannabichromevarin (CBCV), cannabigerovarin (CBGV), cannabigerol monomethyl ether (CBGM), derivatives thereof, salts thereof and any combination thereof. Each possibility represents a separate embodiment of the invention.

In certain embodiments, the cannabinoid is THC or a salt thereof. In certain embodiments, the cannabinoid is CBD or a salt thereof. In certain embodiments, the cannabinoid comprises a mixture of THC or a salt thereof and CBD or a salt thereof.

In certain embodiments, the pharmaceutical composition further comprises at least one N-acylethanolamine. In certain embodiments, the N-acylethanolamine is selected from the group consisting of N-palmitoylethanolamine (PEA), Me-palmitoylethanolamide (Me-PEA), palmitoylcyclohexamide, palmitoylbutylamide, palmitoylisopropylamide, oleoylethanolamine (OEA), palmitoylisopropylamide (PIA), derivatives thereof, salts thereof and any combination thereof. Each possibility represents a separate embodiment of the invention. In certain embodiments, the N-acylethanolamine is PEA or a salt thereof.

The term "N-acylethanolamine" as used herein generally refers to a type of fatty acid amide, lipid-derived signaling molecules, formed when one of several types of acyl group is linked to the nitrogen atom of ethanolamine. These amides conceptually can be formed from a fatty acid and ethanolamine with the release of a molecule of water, but the known biological synthesis uses a specific phospholipase D to cleave the phospholipid unit from N-acylphosphatidylethanolamines. The suffixes—amine and—amide in these names each refer to the single nitrogen atom of ethanolamine that links the compound together: it is termed "amine" in ethanolamine because it is considered as free terminal nitrogen in that subunit, while it is termed "amide" when it is considered in association with the adjacent carbonyl group of the acyl subunit. Names for these compounds may be encountered with either "amide" or "amine" in the present application. The term "ethanolamine" is used in the generic sense and is meant to include mono-ethanolamine, di-ethanolamine, tri-ethanolamine, and mixtures thereof.

The term "derivative" as used herein means a compound whose core structure is the same as, or closely resembles that of an N-acylethanolamine compound, which has a chemical or physical modification, such as different or additional side groups.

The term "salt" as used herein refers to any form of an active ingredient in which the active ingredient assumes an ionic form and is coupled to a counter ion (a cation or anion) or is in solution. This also includes complexes of the active ingredient with other molecules and ions, in particular complexes which are complexed by ion interaction.

In certain embodiments, the N-acylethanolamine comprises a side chain length of 16 carbon units namely palmitoylethanolamide. In other certain embodiments, the N-acylethanolamine is selected from the group consisting of decanoylethanolamide (C10:0), lauroylethanolamide (C12:0), and myristoylethanolamide (C14:0). Each possibility represents a separate embodiment of the present invention.

In some embodiments, the N-acylethanolamine is an N-15 acylethanolamine derivative (see WO 2010/013240). In some embodiments, the N-acylethanolamine is a derivative of N-palmitoylethanolamine. In some embodiments, the ethanolamide group of palmitoylethanolamine is replaced in the derivative with a moiety selected from the group consisting of butylamide, isopropylamide, cyclohexamide, and (2-methyl) ethanolamide. Each possibility represents a separate embodiment of the present invention.

In some embodiments, the N-acylethanolamine is selected from the group consisting of N-palmitoylethanolamine (PEA), Me-palmitoylethanolamide (Me-PEA), palmitoylcyclohexamide, palmitoylbutylamide, palmitoylisopropylamide, oleoylethanolamine (OEA), palmitoylisopropylamide (PIA), derivatives thereof, and salts thereof. Each possibility represents a separate embodiment of the present invention. In certain embodiments, the N-acylethanolamine is PEA.

In some embodiments, the N-acylethanolamine is oleoylethanolamine (OEA) or a derivative thereof. In some embodiments, the ethanolamide group of OEA is replaced in the derivative with a moiety selected from the group consisting of butylamide, isopropylamide, cyclohexamide and (2-methyl) ethanolamide. Each possibility represents a separate embodiment of the present invention. OEA, its derivatives, and methods for synthesizing same are well known in the art, and are described, inter alia, in U.S. Pat. Nos. 6,656,972 and 7,348,338, and United States patent application publication No. 2002/0173550.

In certain embodiments, the N-acylethanolamine is selected from the group consisting of N-palmitoylethanolamine (PEA), Me-palmitoylethanolamide (Me-PEA), palmitoylcyclohexamide, palmitoylbutylamide, palmitoylisopropylamide, oleoylethanolamine (OEA), palmitoylisopropylamide (PIA), derivatives thereof, salts thereof and any combination thereof. In certain embodiments, the N-acylethanolamine is a salt of PEA.

In certain embodiments, the anti-microbial efficacy of the pharmaceutical composition and the same pharmaceutical composition without the cannabinoid are determined against the same bacteria, wherein the bacteria are selected from the group consisting of gentamicin-sensitive *Staphylococcus aureus* ATCC strain 25923, methicillin-resistant *Staphylococcus aureus* and *Streptococcus pneumoniae*. Each possibility represents a separate embodiment of the invention.

In certain embodiments, the pharmaceutically acceptable carrier is suitable for a route of administration selected from the group consisting of oral, topical, mucosal, nasal, rectal, sublingual, parenteral, intravenous, intramuscular, and subcutaneous administration. Each possibility represents a separate embodiment of the invention. In certain embodiments, the pharmaceutically acceptable carrier is suitable for intravenous administration. In certain embodiments, the pharmaceutically acceptable carrier is suitable for intramuscular administration. In certain embodiments, the pharmaceutically acceptable carrier is suitable for oral administration.

The present invention further provides, in another aspect, a pharmaceutical composition as described above, for use in treating or preventing an infectious condition amenable to treatment by an antimicrobial agent.

The phrase "amenable to treatment by antimicrobial agent", refers to any infectious disease or condition that is susceptible to any antimicrobial treatment, may be treated with any antimicrobial treatment and/or known to be treated by any antimicrobial treatments.

The term "treating" as used herein, includes, but is not limited to, any one or more of the following: abrogating, ameliorating, inhibiting, attenuating, blocking, suppressing, reducing, delaying, halting, alleviating or preventing one or more symptoms or side effects of a disease or condition.

The term "acute" refers to a condition with a relatively short, severe course.

The term "chronic" as used herein means that the length of time of the diseases or conditions of the invention can be weeks, months, or possibly years. The intensity of the diseases or conditions can differentiate according to various conditions such as patient age, temperature, season, type of disease, etc.

In certain embodiments, the condition is an infection. In certain embodiments, the microbial infection is in the form of a biofilm. In certain embodiments, the infection is caused by bacteria, mycobacteria or fungi. In certain embodiments, the microbial infection is a bacterial infection. In certain embodiments, the infection is either primary or opportunistic. In certain embodiments, infections can be classified by the anatomic location or organ system infected, including: urinary tract infection, skin infection, respiratory tract infection, odontogenic infection, vaginal infections, and intra-amniotic infections. In addition, locations of inflammation where infection is the most common cause include pneumonia, meningitis and salpingitis.

In certain embodiments, the condition is a side effect associated with antibiotic use. In certain embodiments, the antibiotic use related side effect is range from mild to very serious depending on the antibiotics used, the microbial organisms targeted, and the individual patient. Side effects may reflect the pharmacological or toxicological properties of the antibiotic or may involve hypersensitivity reactions or anaphylaxis. Adverse effects range from fever and nausea to major allergic reactions, including photo-dermatitis and anaphylaxis. Common side-effects include diarrhea, resulting from disruption of the species composition in the intestinal flora, resulting, for example, in overgrowth of pathogenic bacteria, such as *Clostridium difficile*. Anti-bacterial agents can also affect the vaginal flora and may lead to overgrowth of yeast species of the genus *Candida* in the vulvo-vaginal area. Additional side-effects can result from interaction with other drugs, such as elevated risk of tendon damage from administration of a quinolone antibiotic with a systemic corticosteroid.

The present invention further provides, in another aspect, a pharmaceutical composition as described above, for use in treating or preventing a microbial infection or a microbial biofilm.

The term "biofilm" as used herein generally refers to structures, forming on living or non-living surfaces, by any group of microorganisms in which cells stick to each other and often adhere to a surface. These adherent cells are frequently embedded within a self-produced matrix of extracellular polymeric substance (EPS). The microbial cells growing in a biofilm are physiologically distinct from cells of the same organism, which, by contrast, are single-cells that may float or swim in a liquid medium. Infectious processes in which biofilms have been implicated include common problems such as bacterial vaginosis, urinary tract infections, catheter infections, middle-ear infections, formation of dental plaque, gingivitis, coating contact lenses, and less common but more lethal processes such as endocarditis, infections in cystic fibrosis, and infections of permanent indwelling devices such as joint prostheses and heart valves.

In certain embodiments, the microbial infection or microbial biofilm is a bacterial infection or bacterial biofilm.

In certain embodiments, the classic symptoms of a bacterial infection are localized redness, heat, edema, swelling and pain. One of the hallmarks of a bacterial infection is local pain, pain that is in a specific part of the body. For example, if a cut occurs and is infected with bacteria, pain occurs at the site of the infection. Bacterial throat pain is often characterized by more pain on one side of the throat. An ear infection is more likely to be diagnosed as bacterial if the pain occurs in only one ear. A cut that produces pus and milky-colored liquid is most likely infected.

In certain embodiments, the use creates or extends the susceptibility of the microbe to the anti-microbial agent compared to the susceptibility of the microbe to the anti-microbial agent without the at least one cannabinoid. In certain embodiments, the use creates or extends the susceptibility of the microbe to the anti-microbial agent compared to the susceptibility of the microbe to the anti-microbial agent without the at least one cannabinoid and without the at least one N-acylethanolamine.

In certain embodiments, the use is associated with a reduced side effect compared to the use of the at least one anti-microbial agent without the at least one cannabinoid. In certain embodiments, the use is associated with a reduced side effect compared to the use of the at least one anti-microbial agent without at least one cannabinoid and the at least one N-acylethanolamine.

In certain embodiments, the side effect is selected from the group consisting of hypersensitivity towards the at least one anti-microbial agent, an allergic reaction to the at least one anti-microbial agent, fever, nausea, diarrhea and any combination thereof. Each possibility represents a separate embodiment of the invention.

In certain embodiments, the use is associated with increased anti-microbial activity compared to the use of the at least one anti-microbial agent without the at least one cannabinoid. In certain embodiments, the use is associated with increased anti-microbial activity compared to the use of the at least one anti-microbial agent without the at least one cannabinoid and the at least one N-acylethanolamine.

In certain embodiments, the use is associated with a reduced dosage of the at least one anti-microbial agent compared to the use of the at least one anti-microbial agent without the at least one cannabinoid. In certain embodiments, the use is associated with a reduced dosage of the at least one anti-microbial agent compared to the use of the at least one anti-microbial agent without the at least one cannabinoid and the at least one N-acylethanolamine.

In certain embodiments, the use is associated with an extended therapeutic window of the at least one anti-microbial agent compared to the use of the at least one anti-microbial agent without the at least one cannabinoid. In certain embodiments, the use is associated with an extended therapeutic window of the at least one anti-microbial agent compared to the use of the at least one anti-microbial agent without the at least one cannabinoid and the at least one N-acylethanolamine.

The phrase "cannabinoid and cannabinoid-like compounds increase the potency of the antimicrobial agent" as used herein refers to the significantly improved antimicrobial effect of the antimicrobial agent when administered with a cannabinoid with or without an N-acylethanolamine, compared to the therapeutic effect of the antimicrobial agent when administered without the cannabinoid and/or N-acylethanolamine.

The phrase "cannabinoid and cannabinoid-like compounds decreases the required dosage of the antimicrobial agent" as used herein refers to the significantly lower dosage required to achieve a certain antimicrobial effect of the antimicrobial agent when administered with a cannabinoid with or without an N-acylethanolamine, compared to the antimicrobial agent dosage required to achieve the same antimicrobial effect when the antimicrobial agent is administered without the cannabinoid and/or N-acylethanolamine.

The phrase "cannabinoid and cannabinoid-like compounds reduce at least one of the side effects of the antimicrobial agent" as used herein refers to the significantly lower occurrence or severity of at least one of the side effects of the antimicrobial agent when the antimicrobial agent is administered with a cannabinoid with or without an N-acylethanolamine, compared to the severity of the same side effect when the antimicrobial agent is administered without the cannabinoid and/or N-acylethanolamine.

The phrase "cannabinoid and cannabinoid-like compounds prolong the therapeutic window of the antimicrobial agent" as used herein refers to the significantly longer period in which the antimicrobial agent has an antimicrobial effect when administered with a cannabinoid with or without an N-acylethanolamine, compared to the period in which the antimicrobial agent has an antimicrobial effect when administered without the cannabinoid and/or N-acylethanolamine.

In certain embodiments, the microbial infection or the microbial biofilm is selected from the group consisting of a *Staphylococcus* spp. infection or biofilm (including *Staphylococcus aureus* infection or biofilm and *S. epidermidis* infection or biofilm), *Pseudomonas aeruginosa* infection or biofilm, *Porphyromonas* spp. infection or biofilm (including *P. gingivalis* infection or biofilm), *Moraxella* spp. infection or biofilm, *Peptostreptococcus* spp. infection or biofilm, *Enterococcus* spp. infection or biofilm, *Escherichia coli* infection or biofilm, *Klebsiella* infection or biofilm, Streptococcal infection or biofilm, *Treponema pallidum* subspecies *pallidum* infection or biofilm, and *Borrelia* infection or biofilm. Each possibility represents a separate embodiment of the invention.

The present invention further provides, in another aspect, a method of treating or preventing a microbial infection or a microbial biofilm in a subject in need thereof, the method comprising the step of administering to the subject a combination of a first pharmaceutical composition comprising at least one anti-microbial agent and a second pharmaceutical composition comprising at least one cannabinoid, wherein the anti-microbial efficacy of the combination is similar to, or better than, the anti-microbial efficacy of the same first pharmaceutical composition comprising 2 to 150 times the amount of the anti-microbial agent, without the second pharmaceutical composition comprising the at least one cannabinoid, thereby treating or preventing said microbial infection or microbial biofilm.

In certain embodiments, the method further comprises the step of administering to the subject a pharmaceutical composition comprising at least one N-acylethanolamine.

In certain embodiments, the route of administration is selected from the group consisting of oral, topical, mucosal, nasal, rectal, sublingual, parenteral, intravenous, intramuscular and subcutaneous administering. In certain embodiments, an aminoglycoside is administered intravenously, intramuscularly, topically, orally or in a nebulized form. In certain embodiments, penicillin is administered intravenously, intramuscularly or orally. Each possibility represents a separate embodiment of the invention.

In certain embodiments, the subject is a human.

In certain embodiments, the amounts of the anti-microbial agent and of the cannabinoid are sufficient to reach a concentration of at least 0.0005 mg/mL gentamicin and at least 0.0001 mg/mL THC in the subject. In certain embodiments, the amounts of the anti-microbial agent and of the cannabinoid are sufficient to reach a concentration of at least 0.0001 mg/mL gentamicin and at least 0.0005 mg/mL THC in the subject.

In certain embodiments, the amounts of the anti-microbial agent and of the cannabinoid are sufficient to reach a concentration of at least 0.0002 mg/mL gentamicin and at least 0.0005 mg/mL THC in the subject. In certain embodiments, the amounts of the anti-microbial agent and of the cannabinoid are sufficient to reach a concentration of at least 0.00003 mg/mL gentamicin and at least 0.001 mg/mL THC in the subject.

In certain embodiments, the amounts of the anti-microbial agent and of the cannabinoid are sufficient to reach a concentration of at least 0.0313 mg/mL gentamicin and at least 0.0005 mg/mL THC in the subject. In certain embodiments, the amounts of the anti-microbial agent and of the cannabinoid are sufficient to reach a concentration of at least 0.0078 mg/mL gentamicin and at least 0.001 mg/mL THC in the subject.

In certain embodiments, the amounts of the anti-microbial agent and of the cannabinoid are sufficient to reach a concentration of at least 0.25 mg/mL ampicillin and at least 0.001 mg/mL THC in the subject.

In certain embodiments, the amounts of the anti-microbial agent and of the cannabinoid are sufficient to reach a concentration of at least 0.0001 mg/mL carbenicillin and at least 0.0005 mg/mL THC in the subject.

In certain embodiments, the amounts of the anti-microbial agent and of the cannabinoid are sufficient to reach a concentration of at least 0.0002 mg/mL gentamicin and at least 0.002 mg/mL THC in the subject.

The present invention further provides, in another aspect, a kit, the kit comprising (a) a first pharmaceutical composition comprising at least one anti-microbial agent and (b) a second pharmaceutical composition comprising at least one cannabinoid.

In certain embodiments, the kit further comprises a third pharmaceutical composition comprising at least one N-acylethanolamine.

In certain embodiments, the at least one anti-microbial agent and the at least one cannabinoid are non-natural. In certain embodiments, the at least one anti-microbial agent, the at least one cannabinoid and the at least one N-acylethanolamine are non-natural. In certain embodiments, the kit is for use in treating or preventing a microbial infection or biofilm formation.

The present invention further provides, in another aspect, a pharmaceutical composition comprising at least one anti-microbial agent, a pharmaceutical composition comprising at least one cannabinoid and a pharmaceutical composition comprising at least one N-acylethanolamine, for use in treating or preventing a microbial infection or biofilm formation.

The present invention further provides, in another aspect, a method of treating or preventing an infectious condition or disease amenable to treatment by an antimicrobial agent in a subject in need thereof, the method comprising the step of administering to the subject a pharmaceutical composition comprising at least one anti-microbial agent and a pharmaceutical composition comprising at least one at least one cannabinoid, thereby treating or preventing said infectious condition or disease.

The terms "Multi-drug resistance (MDR)" and "Antimicrobial resistance (AMR)" as used herein generally refer to the evolution of the bacterial organism to become more or fully resistant to antimicrobials which previously could treat it. This term also encompasses antibiotic resistance, which applies to bacteria and antibiotics. Resistance usually arises through one of three ways: natural resistance in certain types of bacteria; genetic mutation; or by one species acquiring resistance from another. Resistance may appear spontaneously due to random mutations; or more commonly following gradual buildup over time, and because of misuse of antibiotics or antimicrobials.

The term "topical" as used herein refers to the application of a composition according to the invention directly onto at least a portion/region of a subject's skin (human's or non-human's skin) so as to achieve a desired effect, for example, treating dermatological diseases as described herein.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

The term "mucosal administration" relates to delivery of a composition to a mucous membrane, such as the buccal or labial mucosa or the mucosa of the respiratory tract, such as the nasal mucosa.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries as desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, and sodium carbomethyl-cellulose; and/or physiologically acceptable polymers such as polyvinylpyrrolidone (PVP). If desired, disintegrating agents, such as cross-linked polyvinyl pyrrolidone, agar, or alginic acid or a salt thereof, such as sodium alginate, may be added.

The term "oral administration" refers to any method of administration in which an active agent can be administered by swallowing, chewing, sucking, or drinking an oral dosage form. Examples of solid dosage forms include conventional tablets, multi-layer tablets, capsules, caplets, etc., which do not substantially release the drug in the mouth or in the oral cavity.

Dragee cores are provided with suitable coatings. For this purpose, concentrated sugar solutions may be used which may optionally contain gum arabic, talc, polyvinyl pyrrolidone, CARBOPOL gel, polyethylene glycol, titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions that can be used orally include stiff or soft, sealed capsules made of gelatin and a plasticizer, such as glycerol or sorbitol. The capsules may contain the active ingredients in admixture with filler such as lactose, binders such as starches, lubricants such as talc or magnesium stearate, and, optionally, stabilizers.

In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal and sublingual administration, the compositions may take the form of tablets or lozenges formulated in conventional manner or in adhesive carriers.

The pharmaceutical composition described herein may be formulated for parenteral administration, e.g., by bolus injection or continuous infusion. Formulations for injection may be presented in unit dosage form, e.g., in ampoules or in multidose containers with, optionally, an added preservative. The compositions may be suspensions, solutions, or emulsions in oily or aqueous vehicles, and may contain formulatory agents such as suspending, stabilizing, and/or dispersing agents.

Pharmaceutical compositions for parenteral administration include aqueous solutions of the active preparation in water-soluble form. Additionally, suspensions of the active ingredients may be prepared as appropriate oily or water-based injection suspensions. Suitable lipophilic solvents or vehicles include fatty oils such as sesame oil, or synthetic fatty acid esters such as ethyl oleate, triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the active ingredients, to allow for the preparation of highly concentrated solutions.

Alternatively, the active ingredient may be in powder form for constitution with a suitable vehicle, e.g., a sterile, pyrogen-free, water-based solution, before use.

The present compositions can also be delivered using an in-situ formed depot (ISFD). Examples of in situ formed depots include semi-solid polymers which can be injected as a melt and form a depot upon cooling to body temperature. The requirements for such ISFD include low melting or glass transition temperatures in the range of 25-658° C. and an intrinsic viscosity in the range of 0.05-0.8 dl/g. Below the viscosity threshold of 0.05 dl/g no delayed diffusion could be observed, whereas above 0.8 dl/g the ISFD was no longer injectable using a needle. At temperatures above 378° C. but below 658° C. these polymers behave like viscous fluids which solidify to highly viscous depots. Drugs are incorporated into the molten polymer by mixing without the application of solvents. Thermoplastic pastes (TP) can be used to generate a subcutaneous drug reservoir from which diffusion occurs into the systemic circulation. In situ cross-linked polymer systems utilize a cross-linked polymer network to control the diffusion of macromolecules over a prolonged period of time. Use of in situ cross-linking implants necessitates protection of the bioactive agents during the cross-linking reaction. This could be achieved by encapsulation into fast degrading gelatin microparticles.

An ISFD can also be based on polymer precipitation. A water-insoluble and biodegradable polymer is dissolved in a biocompatible organic solvent to which a drug is added forming a solution or suspension after mixing. When this formulation is injected into the body the water miscible organic solvent dissipates and water penetrates into the organic phase. This leads to phase separation and precipitation of the polymer forming a depot at the site of injection. One example of such a system is ATRIGELE™ (ARTIX Laboratories).

Thermally induced gelling systems can also be used as ISFDs. Numerous polymers show abrupt changes in solubility as a function of environmental temperature. The prototype of a thermosensitive polymer is poly(N-isopropyl acryl amide), poly-NIPAAM, which exhibits a rather sharp lower critical solution temperature.

Thermoplastic pastes such as the new generation of poly(ortho esters) developed by AP Pharma can also be used for depot drug delivery. Such pastes include polymers that are semi-solid at room temperature, hence heating for drug incorporation and injection is no longer necessary. Injection is possible through needles no larger than 22 gauge. The drug can be mixed into the systems in a dry and, therefore, stabilized state. Shrinkage or swelling upon injection is thought to be marginal and, therefore, the initial drug burst is expected to be lower than in the other types of ISFD. An additional advantage is afforded by the self-catalyzed degradation by surface erosion.

The compositions of the present invention can also be delivered from medical devices, such as orthopedic implants, contact lenses, micro needle arrays, patches and the like.

Sustained-release (SR), extended-release (ER, XR, or XL), time-release or timed-release, controlled-release (CR), or continuous-release (CR or Contin) pills are tablets or capsules formulated to dissolve slowly and release a drug over time. Sustained-release tablets are formulated so that the active ingredient is embedded in a matrix of insoluble substance (e.g. acrylics, polysaccharides etc.) such that the dissolving drug diffuses out through the holes in the matrix. In some SR formulations the matrix physically swells up to form a gel, so that the drug has first to dissolve in matrix, then exit through the outer surface. Difference between controlled release and sustained release is that controlled release is perfectly zero order release that is, the drug releases with time irrespective of concentration. On the other hand, sustained release implies slow release of the drug over a time period. It may or may not be controlled release.

Pharmaceutical compositions suitable for use in the context of the present invention include compositions wherein the active ingredients are contained in an amount effective to achieve the intended purpose. More specifically, a "therapeutically effective amount" means an amount of active ingredients effective to prevent, alleviate, or ameliorate a symptom or side effect of a disease or disorder, or prolong the survival of the subject being treated. Determination of a therapeutically effective amount is well within the capability of those skilled in the art, especially in light of the detailed disclosure provided herein.

For any preparation used in the methods of the invention, the dosage or the therapeutically effective amount can be estimated initially from in vitro and cell culture assays. For example, a dose can be formulated in animal models to achieve a desired concentration or titer. Such information can be used to more accurately determine useful doses in humans.

The dosage of each compound of the claimed combinations depends on several factors, including: the administration method, the disease to be treated, the severity of the disease, whether the disease is to be treated or prevented, and the age, weight, and health of the person to be treated. Additionally, pharmacogenomic (the effect of genotype on the pharmacokinetic, pharmacodynamic or efficacy profile of a therapeutic) information about a particular patient may affect dosage used.

Continuous daily dosing may not be required; a therapeutic regimen may require cycles, during which time a drug is not administered, or therapy may be provided on an as-needed basis during periods of acute disease worsening.

Dosage escalation may or may not be required; a therapeutic regimen may require reduction in medication dosage.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration, and dosage can be chosen by the individual physician in view of the patient's condition. (See, e.g., Fingl, E. et al., 1975, "The Pharmacological Basis of Therapeutics," Ch. 1, p. 1.) Depending on the severity and responsiveness of the condition to be treated, dosing can be of a single or a plurality of administrations, with course of treatment lasting from several days to several weeks, or until cure is achieved or diminution of the disease state is achieved.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser device may also be accompanied by a notice in a form prescribed by a governmental agency regulating the manufacture, use, or sale of pharmaceuticals, which notice is reflective of approval by the agency of the form of the compositions for human or veterinary administration. Such notice, for example, may include labeling approved by the U.S. Food and Drug Administration (FDA) for prescription drugs or of an approved product insert. Compositions comprising a preparation of the invention formulated in a pharmaceutically acceptable carrier may also be prepared, placed in an appropriate container, and labeled for treatment of an indicated inflammatory disorder, as further detailed above.

In certain embodiments, the cannabinoid increases the potency of the antibiotic compared to the same pharmaceutical composition without the antibiotic. In certain embodiments, the cannabinoid decreases the required dosage of the antibiotic compared to the same pharmaceutical composition without the cannabinoid. In certain embodiments the cannabinoid reduces at least one of the side effects of the antibiotic compared to the same pharmaceutical composition without the cannabinoid. In certain embodiments, the cannabinoid prolongs the therapeutic window of the antibiotic compared to the same pharmaceutical composition without the cannabinoid. In certain embodiments, the composition of the cannabinoid and the N-acylethanolamine increases the potency of the antibiotic compared to the same pharmaceutical composition without the cannabinoid and the N-acylethanolamine. In certain embodiments, the composition of the cannabinoid and the N-acylethanolamine decreases the required dosage of the antibiotic compared to the same pharmaceutical composition without the cannabinoid and the N-acylethanolamine. In certain embodiments, the composition of the cannabinoid and the N-acylethanolamine reduces at least one of the side effects of the antibiotic compared to the same pharmaceutical composition without the cannabinoid and the N-acylethanolamine. In certain embodiments, the composition of the cannabinoid and the N-acylethanolamine prolongs the therapeutic window of the antibiotic compared to the same pharmaceutical composition without the cannabinoid and the N-acylethanolamine.

In certain embodiments, the route of administering is independently selected for each drug from the group consisting of oral, topical, mucosal, nasal, rectal, sublingual, parenteral, intravenous, intramuscular, and subcutaneous administering. Each possibility represents a separate embodiment of the invention.

In certain embodiments of the method described above, the antibiotic and the cannabinoid are comprised in the same pharmaceutical composition. In certain embodiments of the method described above, the antibiotic, the cannabinoid and the N-acylethanolamine are comprised in the same pharmaceutical composition.

The present invention further provides, in an aspect, a dosage unit, comprising or consisting of any one of the pharmaceutical compositions described above.

In certain embodiments, the dosage unit comprises 10-500 µg cannabinoid. In certain embodiments, the dosage unit comprises 0.5-50 mg cannabinoid. In certain embodiments, the cannabinoid is THC. In certain embodiments, the dosage unit is formulated for a route of administration selected from the group consisting of inhalation, topical, mucosal, nasal, oral, rectal, sublingual, parenteral, intravenous, intramuscular, and subcutaneous administration.

The present invention further provides, in another aspect, a method of enhancing the efficacy of an anti-bacterial agent in a patient in need of anti-bacterial treatment, comprising co-administering at least one anti-bacterial agent and at least one cannabinoid to the patient.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

Example 1. PEA Synergistically Reduces the Effective Concentration of THC

The goal of the current experiment was to determine the minimal bactericidal concentrations (MBC) for THC with and without PEA on S. Aureus ATCC strain 25923 (gentamicin-sensitive).

Protocol:

1. Incubation of the S. aureus (from a −80° C. stock) in 3 ml Muller Hinton (MH, Difco) medium at 37° C. under agitation of 250 rpm for 18-20 hours (this culture served as a starter for the experiment);

2. Dilution of the starter culture using saline to obtain working cultures of $5*10^5$ and $10^6$ C.F.U/mL bacteria, respectively.

3. Diluting the THC (0.125 mg/mL in saline) with or without PEA or gentamicin in a 96-well plate.

4. Incubation of the plates at 37° C. under shaking (100 rpm) for 18-20 hours.

5. In the following day, the bacteria in the wells suspended in saline were evaluated for their C.F.U/mL to determine the MBC.

Results: The MBC value for THC alone was found to be about 0.0078 mg/ml, a 32-fold decrease compared to the MBC value for gentamicin alone (0.25 mg/ml), while the MBC value for THC in combination with PEA was found to be about 0.0019 mg/ml, a further 4-fold decrease compared to the MBC value for THC alone (FIG. 1).

Example 2. THC Synergistically Reduces the Effective Concentration of Gentamicin The goal of the current experiment was to determine the minimal inhibitory concentration (MIC) for gentamicin with and without THC on S. Aureus ATCC strain 25923 (gentamicin-sensitive). The cutoff value to determine the MIC was set to an optical density (OD) value of ≤0.1. The results are summarized in FIG. 2.

Results: The MIC value for THC alone was found to be about 0.001 mg/mL, while the MIC value for gentamicin alone was also found to be about 0.001 mg/mL. However, the MIC value for gentamicin was synergistically reduced by 4-fold to 16-fold in combination with THC compared to gentamicin alone (0.0005 mg/mL Gen.+0.0001 mg/mL THC; 0.0001 mg/mL Gen.+0.0005 mg/mL THC).

Example 3. THC Synergistically Reduces the Effective Concentration of Gentamicin The goal of the current experiment was to determine the minimal inhibitory concentration (MIC) for gentamicin with and without THC on S. Aureus ATCC strain 25923 (gentamicin-sensitive). The cutoff value to determine the MIC was set to an optical density (OD) value of ≤0.1. The results are summarized in FIG. 3.

Results: The MIC value for THC alone was found to be about 0.002 mg/mL, while the MIC value for gentamicin alone was also found to be about 0.002 mg/mL. However, the MIC value for gentamicin was synergistically reduced by 4-fold to 64-fold in combination with THC compared to gentamicin alone (0.0002 mg/mL Gen.+0.0005 mg/mL THC; 0.00003 mg/mL Gen.+0.001 mg/mL THC).

Example 4. THC Synergistically Reduces the Effective Concentration of Gentamicin The goal of the current experiment was to determine the minimal inhibitory concentration (MIC) for gentamicin with and without THC on methicillin-resistant *Staphylococcus aureus* (MRSA), which is a multi-drug-resistant strain of *S. aureus*. The cutoff value to determine the MIC was set to an optical density (OD) value of ≤0.1. The results are summarized in FIG. 4.

Results: The MIC value for THC alone was found to be about 0.002 mg/mL, while the MIC value for gentamicin alone was found to be about 0.125 mg/mL. However, the MIC value for gentamicin was synergistically reduced by 4-fold to 16-fold in combination with THC compared to gentamicin alone (0.0313 mg/mL Gen.+0.0005 mg/mL THC; 0.0078 mg/mL Gen.+0.001 mg/mL THC).

TABLE 1

|  | THC | Gen. | THC + Gen. |
| --- | --- | --- | --- |
| MRSA | 0.001953 | 0.125 | 0.000977 THC + 0.0078125 Gen. 0.000488 THC + 0.03125 Gen. |

Example 5. THC Synergistically Reduces the Effective Concentration of Ampicillin The goal of the current experiment was to determine the minimal inhibitory concentration (MIC) for ampicillin with and without THC on methicillin-resistant *Staphylococcus aureus* (MRSA). The cutoff value to determine the MIC was set to an optical density (OD) value of ≤0.1. The results are summarized in FIG. 5.

Results: The MIC value for THC alone was found to be about 0.002 mg/mL, while the MIC value for ampicillin alone was found to be about 0.5 mg/mL. However, the MIC value for ampicillin was synergistically reduced by 2-fold in combination with THC compared to ampicillin alone (0.25 mg/mL Amp.+0.001 mg/mL THC).

Example 6. THC Synergistically Reduces the Effective Concentration of Carbenicillin The goal of the current experiment was to determine the minimal inhibitory concentration (MIC) for carbenicillin with and without THC on *Streptococcus pneumoniae*. The cutoff value to determine the MIC was set to an optical density (OD)

value of ≤0.1. The results are summarized in FIG. 6.

Results: The MIC value for THC alone was found to be about 0.002 mg/mL, while the MIC value for carbenicillin alone was found to be about 0.0002 mg/mL. However, the MIC value for carbenicillin was synergistically reduced by 2-fold in combination with THC compared to carbenicillin alone (0.0001 mg/mL Carb.+0.0005 mg/mL THC).

Example 7. CBG Synergistically Reduces the Effective Concentration of Gentamicin The goal of the current experiment was to determine the minimal inhibitory concentration (MIC) for gentamicin with and without CBG on methicillin-resistant *Staphylococcus aureus* (MRSA) and vancomycin-resistant *Staphylococcus aureus* (MRSA) (VISA) clinical strain No 111 from Souraski Medical Center, Tel Aviv, Israel. The cutoff value to determine the MIC was set to an optical density (OD) value of ≤0.1. The results are summarized in Table 2 below.

Results: The MIC value for CBG alone was found to be about 8 μg/mL, while the MIC value for gentamicin alone was found to be about 256 μg/mL. Fractional Inhibitory Concentration values (FicA and FicB) and Fic index were calculated for each combination of compounds and clinical isolate using the following standard equations for this analysis:

Fic index=FicA+FicB

FicA=MIC of compound A (CBG) in combination/MIC of compound A alone.

FicB=MIC of compound B (gentamicin) in combination/MIC of compound B alone.

Synergy is defined as a Fic index value of ≤0.5. Indifference or no interaction will be defined as a FIC index value of >0.5 and <4. Antagonism will be defined as a FIC index value of >4. When the FIC index value is within the range of 0.5-1, the combination is considered to be non-synergistic or additive. The MIC value for gentamicin was synergistically reduced by 4-fold in combination with CBG compared to gentamicin alone (64 μg/mL Gen.+1 μg/mL CBG).

CBG's FicA value was 0.125, while gentamicin FicB value was 0.25. Calculated Fic value, the sum of FicA and FicB, was 0.375. The resulted Fic index value was 50.5, thus synergy was observed.

TABLE 2

|  | CBG μg/mL | Gen. μg/mL | CBG + Gen. μg/mL |
|---|---|---|---|
| MRSA/VISA | 8 | 256 | 1 CBG + 64 Gen.<br>0.5 CBG + 128 Gen. |

Example 8. CBG Synergistically Reduces the Effective Concentration of Gentamicin The goal of the current experiment was to determine the minimal inhibitory concentration (MIC) for gentamicin with and without CBG on methicillin-resistant *Staphylococcus aureus* (MRSA) violent clinical strain 760330509 from Souraski Medical Center, Tel Aviv, Israel. The cutoff value to determine the MIC was set to an optical density (OD) value of ≤0.1. The results are summarized in Table 3 below.

Results: The MIC value for CBG alone was found to be about 8 μg/mL, while the MIC value for gentamicin alone was found to be about 128 μg/mL. Fractional Inhibitory Concentration values (FicA and FicB) and Fic index were calculated for each combination of compounds and clinical isolate using the same calculation as in example 7.

The MIC value for gentamicin was synergistically reduced by 4-fold in combination with CBG compared to gentamicin alone (32 μg/mL Gen.+1 μg/mL CBG).

CBG's FicA value was 0.125, while gentamicin FicB value was 0.25. CBG's FicA value was 0.125, while gentamicin FicB value was 0.25. Calculated Fic value, the sum of FicA and FicB, was 0.375. The resulted Fic index value was ≤0.5, thus synergy was observed.

TABLE 3

|  | CBG μg/mL | Gen. μg/mL | CBG + Gen. μg/mL |
|---|---|---|---|
| MRSA | 8 | 128 | 1 CBG + 32 Gen.<br>0.25 CBG + 64 Gen. |

Example 9. CBD Synergistically Reduces the Effective Concentration of Gentamicin The goal of the current experiment was to determine the minimal inhibitory concentration (MIC) for gentamicin with and without CBD on methicillin-resistant *Staphylococcus aureus* (MRSA) and vancomycin-resistant *Staphylococcus aureus* (MRSA) (VISA) clinical strain No 111 from Souraski Medical Center, Tel Aviv, Israel. The cutoff value to determine the MIC was set to an optical density (OD) value of ≤0.1. The results are summarized in Table 4 below.

Results: The MIC value for CBD alone was found to be about 8 μg/mL, while the MIC value for gentamicin alone was found to be about 256 μg/mL. Fractional Inhibitory Concentration values (FicA and FicB) and Fic index were calculated for each combination of compounds and clinical isolate using the same calculation as in example 7.

The MIC value for gentamicin was synergistically reduced by 8-fold in combination with CBD compared to gentamicin alone (32 μg/mL Gen.+1 μg/mL CBD).

CBD's FicA value was 0.125, while gentamicin FicB value was 0.125. Calculated Fic value, the sum of FicA and FicB, was 0.25. The resulted Fic index value was ≤0.5, thus synergy was observed.

TABLE 4

|  | CBD μg/mL | Gen. μg/mL | CBD + Gen. μg/mL |
|---|---|---|---|
| MRSA/VISA | 8 | 256 | 1 CBD + 3 Gen.<br>1 CBD + 64 Gen. |

Example 10. THC Potentiates Antibiotics to Treat Biofilm

The goal of the current experiment was to determine the minimal inhibitory concentration (MIC) for gentamicin with and without THC on an established S. Aureus ATCC strain 25923 (gentamicin-sensitive) biofilm. The cutoff value to determine the MIC was set to an optical density (OD) value of ≤0.1. The results are summarized in FIG. 7.

Results: The MIC value for THC alone was found to be about 0.004 mg/mL, while the MIC value for gentamicin could not even be determined and apparently was well over 0.002 mg/mL. However, the MIC value for gentamicin was synergistically reduced to 0.0002 mg/mL and lower in combination with THC compared to gentamicin alone (0.0002 mg/mL Gen.+0.002 mg/mL THC).

Example 11. Evaluation of Combinations of Anti-Microbial Agents, Cannabinoids and/or N-Acylethanolamines Against Non-Resistant and Drug-Resistant Strains of Bacteria The purpose of this study is to investigate whether the addition of cannabinoids and/or N-acylethanolamines to anti-microbial agents reduces the minimum inhibitory concentrations (MIC) of the anti-microbial agents towards non-resistant and methicillin-resistant strains of Staphylococcus aureus (MRSA).

Non-resistant, standard S. aureus strain (ATCC 25923) and a clinical resistant MRSA isolate (XU212), are used. Tetracycline, and oxacillin are obtained from Sigma Chemical Co. Oxacillin is used in place of methicillin as recommended by the National Committee for Clinical Laboratory Standards (NCCLS) (NCCLS, Summary Minutes, Subcommittee on Veterinary Antimicrobial Susceptibility Testing, Jan. 18-19, 2007). Mueller-Hinton broth (MHB; Oxoid) is adjusted to contain 20 mg/L $Ca^{2+}$ and 10 mg/L $Mg^{2+}$.

Overnight cultures of each strain are made up in 0.9% saline to an inoculum density of $5 \times 10^5$ colony-forming units (c.f.u.) by comparison with a MacFarland standard. Tetracycline and oxacillin are dissolved directly in MHB, whereas norfloxacin and erythromycin are dissolved in DMSO and then diluted in MHB to give a starting concentration of 512 μg/mL. PEA and A9-tetrahydrocannabinol are dissolved in a vehicle that comprises a mixture of ethanol, alkamuls-620 and MHB at a ratio of 1:1:18. Using Nunc 96-well microtiter plates, 125 μL of MHB is dispensed into wells 1-11. Then, 125 μL of the test compound or the appropriate antibiotic is dispensed into a well and serially diluted across the plate, leaving a well empty for the growth control. The final volume is dispensed into another well, which being free of MHB or inoculum serves as the sterile control. Finally, the bacterial inoculum (125 μL) is added to the wells, and the plate is incubated at 37° C. for 18 hours. A DMSO control (3.125%) is also included. All MICs are determined from duplicate samples. The MIC is determined as the lowest concentration at which no growth was observed. A methanolic solution (5 mg/mL) of 3-[4,5-dimethylthiazol-2-yl]-2,5-diphenyltetrazoliium bromide (MTT; Lancaster) is used to detect bacterial growth by a color change from yellow to blue.

Treatment groups consist of (1) Control, (2) tetracycline, (3) Oxacillin, (4) THC, (5) THC and PEA, (6) tetracycline and THC, (7) tetracycline and THC and PEA, (8) Oxacillin and THC, and (9) Oxacillin and THC and PEA.

Example 12. Evaluation of Combinations of Anti-Microbial Agents, Cannabinoids and/or N-Acylethanolamines Against Biofilm Formation The purpose of the study is to investigate whether the addition of cannabinoids and/or N-acylethanolamines to anti-microbial agents potentiates the anti-microbial agents in preventing and/or eradicating the biofilm.

A variety of pathogenic staphylococcal targets are selected, including non-resistant and MRSA clinical isolates. S. pseudintermedius DK729, S. pseudintermedius DSM21284 and S. intermedius DSM20373 have previously been shown to form biofilms as determined by crystal violet staining (Field et al., 2015). S. aureus SA113 has also demonstrated ability to form strong biofilm (Cramton et al., 1999). Staphylococcus strains are grown in cation-adjusted Mueller Hinton (CA-MH) (Oxoid) for minimum inhibitory concentration assays or Tryptic Soy Broth (TSB) (Merck) supplemented with 1% Glucose at 37° C. for biofilm assays.

Minimum inhibitory concentration determinations are carried out in triplicate in 96-well microtiter plates as described previously (Field et al., 2010, 2012, 2015). Briefly, target strains are grown over night in the appropriate conditions and medium, sub-cultured into fresh broth and allowed to grow to an $OD_{600}$ of 0.5, diluted to a final concentration of $10^5$ c.f.u./ml in a volume of 0.2 ml. penicillin G, ampicillin, streptomycin, erythromycin, and cefuroxime (Sigma) are re-suspended in CA-MH media to a stock concentration of 128 or 256 μg/ml. The antibiotics are adjusted to 16, 32, or 64 g/ml starting concentration and two-fold serial dilutions of each compound are made in 96-well plates for a total of 12 dilutions. The target strain is then added and after incubation for 16 hours at 37° C. and the MIC is determined as the lowest peptide concentration causing inhibition of visible growth.

Static microtitre plate assays based on a previous study (Kelly et al., 2012), but with modifications to optimize the assay, are used to investigate the biofilm formation and combination treatments. Tryptic Soybean Broth (TSB, Merck) supplemented with 1% D-(C)-glucose (Sigma Aldrich) (TSBg) is used in these assays, which aids in biofilm formation. Briefly, a 1:100 dilution is performed by adding 2 μl of log phase cells ($10^7$ c.f.u/ml of each culture) to 198 μl of TSBg in wells of a sterile 96-well microtiter plate (Sarstedt, Leicester, UK), giving a starting inoculum of $10^5$ c.f.u/ml; 200 ml of TSBg is added to a set of wells as a negative control. All wells are seeded in triplicate. Microtiter plates are then incubated at 37° C. for 48 hours to allow biofilm formation. After biofilms are established and washed once with phosphate buffered saline (PBS), the compounds of interest are added to the microtiter plate wells at 1×, 2×, 4×, 8× and 16×. Following incubation for 24 hours at 37° C., the plates are removed and gently washed once with PBS, then with 100 mL of a solution containing 500 g XTT/L (2,3-bis[2-methyloxy-4-nitro-5-sulfophenyl]-2H-tetrazolium-5-carboxanilide) (Sigma) and 10 mM menadione (Sigma) is added to each well. Microtiter plates are incubated for 2 hours at 37° C. in the dark. Absorbance is measured at 490 nm using a microtiter plate reader (Molecular Devices Spectramax M3, Sunnyvale Calif., USA). Data is obtained in triplicate and calculated and expressed as the mean±SD.

Treatment groups consist of (1) Control, (2) penicillin G, (3) Cefuroxime, (4) THC, (5) THC and PEA, (6) penicillin G and THC, (7) penicillin G and THC and PEA, (8) Cefuroxime and THC, and (9) Cefuroxime and THC and PEA.

Bacteria's staining with crystal violet is performed based on the methods disclosed in Merritt J H et al., Curr. Protoc. Microbiol., 2005. The following strains of bacteria are used in the experiments routine: *Staphylococcus* spp. (including *S. aureus* and *S. epidermidis*), *Pseudomonas aeruginosa*, *Porphyromonas* spp. (especially *P. gingivalis*), *Moraxella* spp., *Peptostreptococcus* spp., and *Enterococcus* spp.

Cells are grown in microtiter dishes for a desired period of time, and then the wells are washed to remove planktonic bacteria. Cells remaining adhered to the wells are subsequently stained with a dye that allows visualization of the attachment pattern. This surface-associated dye can also be solubilized for semi-quantitative assessment of the biofilm formed.

Each bacterium is inoculated in a 3-to-5-mL culture and grown to stationary phase.

Cultures are diluted at 1:100 in the media. 100 µl of each diluted culture is pipetted into each of four wells in a fresh microtiter plate which has not been tissue culture treated. The plate is covered and is incubated at optimal growth temperature for the desired amount of time. Then, 20 µl of 0.1% crystal violet solution (pre-filtered through a 0.44 µm filter) is added to each well and the staining 10 min at room temperature.

Example 13. Evaluation of Cannabinoids and/or n-Acylethanolamines on Side Effects Associated with Anti-Microbial Agents ICR male mice, 8 weeks of age at study initiation are used. The average animal body weight at study initiation is in the range of 24±2 g. The minimum and maximum weight in each group does not exceed ±20% of group mean weight. Animals are randomly allocated to individual cages on the day of reception. Animals are acclimated for seven to nine days.

Animals are divided into 5 experimental groups (6 animals per group):
1. Control/vehicle
2. Penicillin G
3. Penicillin G with THC
4. Penicillin g with THC and PEA
5. THC For the duration of study (2 weeks), animals are given an oral treatment via gavage. Mice are weighted at the beginning of the study and at the day of termination. Clinical signs are monitored daily, including e.g. observation of soft stool (diarrhea), body temperature and occurrence of red or white rash on the animal's legs.

Prior to the experiment the dosage of the antibiotic is titrated, in order to administer tolerable dose, which represents common antibiotic associated side effects, but still void of the respiratory system depression effect. Common side effects of antibiotics in animals include diarrhea, skin rush, fever and body weight gain.

Example 14. THC and/or THC+PEA Combination Synergistically Reduces the Effective Concentration of Antibiotics in Various Strains of Bacteria The following strains of MRSA are assessed: Community-acquired MRSA (such as USA300), Hospital-acquired MRSA, VISA-ATCC 700699, *S. aureus* (strain Mu3/ATCC 700698).

Amongst other bacteria assessed are: *Enterococcus faecium* (*E. faecium*), including clinically relevant strains, and Vancomycin-resistant *Enterococcus* (VRE).

The following antibiotics are examined: Gentamicin, Vancomycin, Daptomycin, Linezolid, Clindamycin, Cephalosporin, TMP/SMZ, and Doxycycline.

In addition, more than one cannabinoid is assessed—CBD, CBN, CBG, THCA and/or THCV.

The methods used are: Micro broth dilution MIC according to CLSI; Synergy evaluation with Checkerboard micro broth dilution MIC and FICI (Fractional Inhibitory Concentration Index Cutoffs) calculation; Evaluation of MBC values of selected specimens in order to assess time-to-kill curve; and/or Crystal violet staining in BKC.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

We claim:

1. A method for treating or preventing a bacterial infection or bacterial biofilm comprising administering a therapeutically effective amount of a pharmaceutical composition comprising at least one anti-bacterial agent, at least one cannabinoid, and a pharmaceutically acceptable carrier, wherein the weight ratio between the at least one anti-bacterial agent, and the at least one cannabinoid is between about 250:1 to about 1:50, wherein the anti-bacterial efficacy of the composition is similar to, or better than the anti-bacterial efficacy of the same composition comprising 2 to 150 times the amount of the at least one anti-bacterial agent without the at least one cannabinoid; wherein the at least one anti-bacterial agent comprises an aminoglycoside; and wherein the at least one cannabinoid is THC or a salt thereof, CBD or a salt thereof, CBG or a salt thereof, or a mixture of THC or a salt thereof and CBD or a salt thereof.

2. The method of claim 1, wherein the at least one anti-bacterial agent is administered intravenously, intramuscularly, topically, orally or in a nebulized form.

3. The method of claim 1, wherein administering the pharmaceutical composition is associated with:
(a) extended the susceptibility of the bacteria to the anti-bacterial agent compared to the susceptibility of the bacteria to the anti-bacterial agent without the at least one cannabinoid;
(b) a reduced side effect compared to administration of the at least one anti-bacterial agent without the at least one cannabinoid, wherein the side effect comprises hypersensitivity towards the at least one anti-bacterial agent, an allergic reaction to the at least one anti-bacterial agent, fever, nausea, diarrhea, or any combination thereof;
(c) increased anti-bacterial activity compared to administration of the at least one anti-bacterial agent without the at least one cannabinoid; and/or
(d) an extended therapeutic window of the at least one anti-bacterial agent compared to administration of the at least one anti-bacterial agent without the at least one cannabinoid.

4. The method of claim 1, wherein the bacterial infection or the bacterial biofilm comprises *Staphylococcus* spp. infection or, *Pseudomonas aeruginosa* infection or biofilm, *Porphyromonas* spp. infection or biofilm, *Moraxella* spp. infection or biofilm, *Peptostreptococcus* spp. infection or biofilm, *Enterococcus* spp. infection or biofilm, *Escherichia coli* infection or biofilm, *Klebsiella* infection or biofilm, Streptococcal infection or biofilm, *Treponema pallidum* subspecies *pallidum* infection or biofilm, and/or *Borrelia* infection or biofilm.

5. A method of treating or preventing a bacterial infection or a bacterial biofilm in a subject in need thereof, comprising administering to the subject a combination of a first pharmaceutical composition comprising at least one anti-bacterial agent and a second pharmaceutical composition comprising at least one cannabinoid, wherein the at least one anti-bacterial agent comprises an aminoglycoside; and wherein the at least one cannabinoid is THC or a salt thereof, CBD or a salt thereof, CBG or a salt thereof, or a mixture of THC or a salt thereof and CBD or a salt thereof, wherein the weight ratio between the at least one anti-bacterial agent, and the at least one cannabinoid is between about 250:1 to about 1:50, wherein the anti-bacterial efficacy of the composition is similar to, or better than the anti-bacterial efficacy of the same composition comprising 2 to 150 times the amount of the at least one anti-bacterial agent without the at least one cannabinoid.

6. The method of claim 5, wherein the at least one anti-bacterial agent is administered intravenously, intramuscularly, topically, orally or in a nebulized form.

7. The method of claim 5, wherein the at least one anti-bacterial agent is administered intravenously, intramuscularly or orally.

8. The method of claim 5, wherein the at least one anti-bacterial agent is administered together or separately with the at least one cannabinoid.

9. The method of claim 2, wherein the aminoglycoside is gentamicin or a salt thereof.

* * * * *